US009546209B2

(12) United States Patent
Aebi et al.

(10) Patent No.: US 9,546,209 B2
(45) Date of Patent: Jan. 17, 2017

(54) TREATMENT OF MUCOSITIS WITH IMMUNOGLOBULIN

(71) Applicants: CSL BEHRING AG, Bern (CH); UNIVERSITAET BERN, Bern (CH)

(72) Inventors: Christoph Aebi, Oberscherli (CH); Sonja Christina Lueer, Bern (CH); Alexander Schaub, Koeniz (CH); Sylvia Miescher, Bern (CH); Adrian Zuercher, Bern (CH); Cédric Pierre Vonarburg, Bern (CH)

(73) Assignees: CSL Behring AG, Bern (CH); Universitaet Bern, Bern (CH)

( * ) Notice: Subject to any disclaimer, the term of this patent is extended or adjusted under 35 U.S.C. 154(b) by 0 days.

(21) Appl. No.: 14/380,457

(22) PCT Filed: Mar. 8, 2013

(86) PCT No.: PCT/EP2013/054722
§ 371 (c)(1),
(2) Date: Aug. 22, 2014

(87) PCT Pub. No.: WO2013/132063
PCT Pub. Date: Sep. 12, 2013

(65) Prior Publication Data
US 2015/0030613 A1 Jan. 29, 2015

(30) Foreign Application Priority Data
Mar. 9, 2012 (EP) ..................... 12158939

(51) Int. Cl.
A61K 39/00 (2006.01)
A61K 39/395 (2006.01)
A61K 49/00 (2006.01)
C07K 16/00 (2006.01)
C07K 16/14 (2006.01)
C07K 16/06 (2006.01)
C07K 16/12 (2006.01)

(52) U.S. Cl.
CPC .............. C07K 16/14 (2013.01); C07K 16/06 (2013.01); C07K 16/065 (2013.01); C07K 16/12 (2013.01); C07K 16/1203 (2013.01); C07K 2317/21 (2013.01); C07K 2317/76 (2013.01)

(58) Field of Classification Search
None
See application file for complete search history.

(56) References Cited

U.S. PATENT DOCUMENTS 6,300,104 B1 * 10/2001 Morrison ......... A61K 39/39591
424/133.1
2010/0322872 A1 * 12/2010 Perraudin ............. A61K 38/40
424/49

FOREIGN PATENT DOCUMENTS

WO  WO 2009/046168 A1    4/2009
WO  WO 2009046168 A1 *  4/2009

OTHER PUBLICATIONS

Keefe et al. 2007 (Updated Clinical Practice Guidelines for the Prevention and Treatment of Mucositis; Cancer 109(5): 820-831).*
Cheng et al. 2001 (Evaluation of an oral care protocol intervention in the prevention of chemotherapy-induced oral mucositis in paediatric cancer patient; European Journal of Cancer 37:2056-2063).*
Phalipon et al. 2002 (Secretory Component: A New Role in Secretory IgA-mediated immune exclusion in vivo; Immunity 17: 107-115).*
Luer et al. 2011 (Topical curcumin can inhibit deleterious effects of upper respiratory tract bacteria on human oropharyngeal cells in vitro: potential role for patients with cancer therapy induced mucositis?; Supportive care in cancer: Official journal of the Multinational Association of Supportive Care in Cancer 19(6):pp. 799-806).*
Morelli et al. 1996 (Oral administration of Anti-Doxorubicin Monoclonal Antibody Prevents Chemotherapy-Induced Gastrointestinal Toxicity in Mice; Cancer Research 56: 2082-2085).*
Balsari et al. 2001 (Topical administration of a doxorubicin-specific monoclonal antibody prevents drug-induced apoptosis in mice; British Journal of Cancer; 85(12): 1964-1967).*
Frese et al. 2007 (Maximizing mouse cancer models; Nature Reviews 7:645-658).*
Balsari et al. 2001 (Topical administration of a doxorubicin-specific monoclonal antibody prevents drug-induced apoptosis in mice; Brit. Journal of Cancer; 85(12): 1964-1967).*
"Prevention and Treatment of Oral Mucositis in Cancer Patients," Best Practice, Evidence Based Practice Information Sheets for Health Professionals, vol. 2, Issue 3, 1998, pp. 1-6.
Aebi et al., "A Protective Epitope of Moraxella catarrhalis Is Encoded by Two Different Genes," Infection and Immunity, vol. 65, No. 11, Nov. 1997, pp. 4367-4377.
Aebi et al., "Phenotypic Effect of Isogenic uspA1 and uspA2 Mutations on Moraxella catarrhalis 035E," Infection and Immunity, vol. 66, No. 7, Jul. 1998, pp. 3113-3119.
Australian Patent Examination Report for Australian Application No. 2013201394, issued Dec. 4, 2013.
Blijlevens et al., "Palifermin (recombinant keratinocyte growth factor-1): a pleiotropic growth factor with multiple biological activities in preventing chemotherapy- and radiotherapy-induced mucositis," Annals of Oncology, vol. 18, No. 5, May 2007 (Published online Oct. 9, 2006), pp. 817-826.
Bootsma et al., "Analysis of Moraxella catarrhalis by DNA Typing: Evidence for a Distinct Subpopulation Associated with Virulence Traits," The Journal of Infectious Diseases, vol. 181, 2000 (Electronically published Apr. 13, 2000), pp. 1376-1387.

(Continued)

Primary Examiner — Gary Nickol
Assistant Examiner — Mary Lyons
(74) Attorney, Agent, or Firm — Birch, Stewart, Kolasch & Birch, LLP

(57) ABSTRACT

The invention relates to compositions comprising immunoglobulin for use in the treatment of mucositis by topical application. In particular, the invention relates to compositions comprising J chain-containing IgA and secretory component for the treatment of mucositis.

28 Claims, 17 Drawing Sheets

(56) References Cited

OTHER PUBLICATIONS

Figure 1:
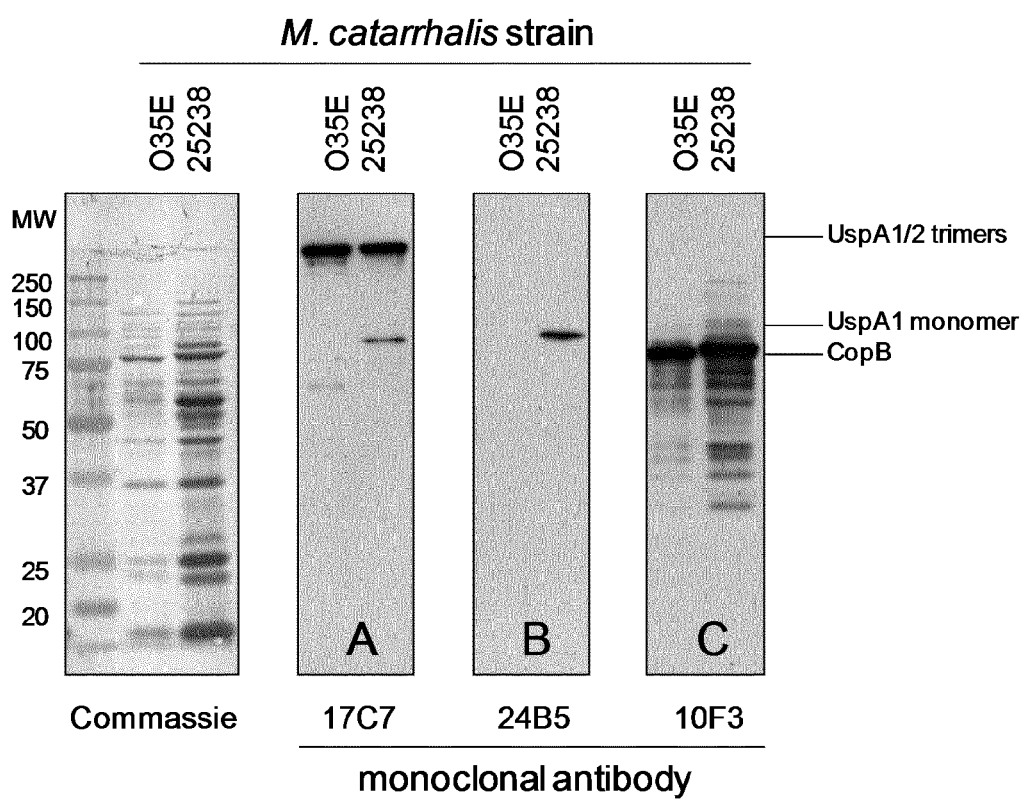

Brach et al., "Ionizing Radiation Induces Expression of Interleukin 6 by Human Fibroblasts Involving Activation of Nuclear Factor-κB," The Journal of Biological Chemistry, vol. 268, No. 12, Apr. 25, 1993, pp. 8466-8472.

Brooks et al., "Moraxella catarrhalis Binding to Host Cellular Receptors Is Mediated by Sequence-Specific Determinants Not Conserved among All UspA1 Protein Variants," Infection and Immunity, vol. 76, No. 11, Nov. 2008 (Published ahead of print on Aug. 4, 2008), pp. 5322-5329.

Cope et al., "Characterization of the Moraxella catarrhalis uspA1 and uspA2 Genes and Their Encoded Products," Journal of Bacteriology, vol. 181, No. 13, Jul. 1999, pp. 4026-4034.

Deshmane et al., "Monocyte Chemoattractant Protein-1 (MCP-1): An Overview," Journal of Interferon and Cytokine Research, vol. 29, No. 6, 2009, pp. 313-326.

Dewhirst et al., "The Human Oral Microbiome," Journal of Bacteriology, vol. 192, No. 19, Oct. 2010 (Published ahead of print on Jul. 23, 2010), pp. 5002-5017.

Donnelly et al., "Antimicrobial therapy to prevent or treat oral mucositis," The Lancet Infectious Diseases, vol. 3, Jul. 2003, pp. 405-412.

Eldika et al., "Role of nontypeable Haemophilus Influenzae in exacerbations and progression of chronic obstructive pulmonary disease," Current Opinion in Pulmonary Medicine, vol. 12, 2006, pp. 118-124.

Elting et al., "The Burdens of Cancer Therapy: Clinical and Economic Outcomes of Chemotherapy-Induced Mucositis," Cancer, vol. 98, No. 7, Oct. 1, 2003, pp. 1531-1539.

Ertugrul et al., "Comparison of CCL28, interleukin-8, interleukin-1 β and tumor necrosis factor-alpha in subjects with gingivitis, chronic periodontitis and generalized aggressive periodontitis," Journal of Periodontal Research, vol. 48, 2013, pp. 44-51.

Extended European Search Report for European Application No. 12158939.4, dated Aug. 17, 2012.

Heiniger et al., "A Reservoir of Moraxella catarrhalis in Human Pharyngeal Lymphoid Tissue," The Journal of Infectious Diseases, vol. 196, Oct. 1, 2007 (Electronically published Aug. 30, 2007), pp. 1080-1087.

Helminen et al., "A Large, Antigenically Conserved Protein on the Surface of Moraxella catarrhalis Is a Target for Protective Antibodies," The Journal of Infectious Diseases, vol. 170, Oct. 1994, pp. 867-872.

Helminen et al., "A Major Outer Membrane Protein of Moraxella catarrhalis Is a Target for Antibodies That Enhance Pulmonary Clearance of the Pathogen in an Animal Model," Infection and Immunity, vol. 61, No. 5, May 1993, pp. 2003-2010.

International Search Report and Written Opinion of the International Searching Authority (Forms PCT/ISA/220, PCT/ISA/210, and PCT/ISA/237) for International Application No. PCT/EP2013/054722, dated May 7, 2013.

Liu et al., "CXCL10/IP-10 in infectious diseases pathogenesis and potential therapeutic implications," Cytokine & Growth Factor Reviews, vol. 22, 2011 (Available online Jul. 29, 2011), pp. 121-130.

Meier et al., "Moraxella catarrhalis strains with reduced expression of the UspA outer membrane proteins belong to a distinct subpopulation," Vaccine, vol. 23, 2005 (Available online Nov. 10, 2004), pp. 2000-2008.

Meier et al., "Salivary Antibodies Directed against Outer Membrane Proteins of Moraxella catarrhalis in Healthy Adults," Infection and Immunity, vol. 71, No. 12, Dec. 2003, pp. 6793-6798.

Monteiro et al., "IgA Fc Receptors," The Annual Review of Immunology, vol. 21, 2003 (First published online as a Review in Advance on Jan. 28, 2003), pp. 177-204.

Mose et al., "Can Prophylactic Application of Immunoglobulin Decrease Radiotherapy-Induced Oral Mucositis?" American Journal of Clinical Oncology, vol. 20, Issue 4, Aug. 1997, pp. 407-411, (enlarged copies of the tables included).

Moura et al., "Identification of the Transferrin Receptor as a Novel Immunoglobulin (Ig)A1 Receptor and Its Enhanced Expression on Mesangial Cells in IgA Nephropathy," The Journal of Experimental Medicine, vol. 194, No. 4, Aug. 20, 2001, pp. 417-425.

Murphy et al., "Isolation of the outer membrane of Branhamella catarrhalis," Microbial Pathogenesis, vol. 6, 1989, pp. 159-174.

Phalipon et al., "Secretory Component: A New Role in Secretory IgA-Mediated Immune Exclusion in Vivo," Immunity, vol. 17, Jul. 2002, pp. 107-115.

Plevová et al., "Intravenous Immunoglobulin as Prophylaxis of Chemotherapy-Induced Oral a Mucositis," Correspondence, Journal of the National Cancer Institute, vol. 89, No. 4, Feb. 19, 1997, pp. 326-327, XP-002680345.

Ponka et al., "The transferrin receptor: role in health and disease," The International Journal of Biochemistry & Cell Biology, vol. 31, 1999, pp. 1111-1137.

Que et al., "Fibrinogen and fibronectin binding cooperate for valve infection and invasion in *Staphylococcus aureus* experimental endocarditis," The Journal of Experimental Medicine, vol. 201, No. 10, May 16, 2005, pp. 1627-1635.

Ratner et al., "Synergistic proinflammatory responses induced by polymicrobial colonization of epithelial surfaces," Proceedings of the National Academy of Sciences, vol. 102, No. 9, Mar. 1, 2005, pp. 3429-3434.

Rincon, "Interleukin-6: from an inflammatory marker to a target for inflammatory diseases," Trends in Immunology, vol. 33, No. 11, Nov. 2012, pp. 571-577.

Ryu et al., "Therapeutic Effects of Recombinant Human Epidermal Growth Factor (rhEGF) in a Murine Model of Concurrent Chemo- and Radiotherapy-Induced Oral Mucositis," Journal of Radiation Research, vol. 51, 2010, pp. 595-601.

Schedler et al., "Treatment of radiogenic mucositis in patients with head and neck tumors with polyvalent intramuscular immunoglobulin," Tumor Diagnostik and Therapie, vol. 15, No. 5, 1994, pp. 184-191, XP009161354.

Sonis, "Mucositis as a biological process: a new hypothesis for the development of chemotherapy-induced stomatotoxicity," Oral Oncology, vol. 34, 1998, pp. 39-43.

Sonis, "Mucositis: The impact, biology and therapeutic opportunities of oral mucositis," Oral Oncology, vol. 45, 2009 (Available online Oct. 13, 2009), pp. 1015-1020.

Spaniol et al., "Outer membrane protein UspA1 and lipooligosaccharide are involved in invasion of human epithelial cells by Moraxella catarrhalis," Microbes and Infection, vol. 10, 2008 (Available online Oct. 2, 2007), pp. 3-11.

Spielberger et al., "Palifermin for Oral Mucositis after Intensive Therapy for Hematologic Cancers," The New England Journal of Medicine, vol. 351, No. 25, Dec. 16, 2004, pp. 2590-2598.

Stokman et al., "Oral mucositis and selective elimination of oral flora in head and neck cancer patients receiving radiotherapy: a double-blind randomised clinical trial," British Journal of Cancer, vol. 88, 2003, pp. 1012-1016.

Suzuki et al., "Autocrine production of epithelial cell-derived neutrophil attractant-78 induced by granulocyte colony-stimulating factor in neutrophils," Blood, vol. 99, No. 5, Mar. 1, 2002, pp. 1863-1865.

The Human Microbiome Project Consortium, "Structure, function and diversity of the healthy human microbiome," Nature, vol. 486, Jun. 14, 2012, pp. 207-214.

Watkins et al., "Attenuation of radiation- and chemoradiation-induced mucositis using gamma-D-glutamyl-L-tryptophan (SCV-07)," Oral Diseases, vol. 16, 2010, pp. 655-660.

Wijers et al., "Mucositis reduction by selective elimination of oral flora in irradiated cancers of the head and neck: A placebo-controlled double-blind randomized study," International Journal of Radiation Oncology Biology Physics, vol. 50, No. 2, 2001, pp. 343-352.

International Preliminary Report on Patentability issued in PCT Application No. PCT/EP2013/054722 on Sep. 18, 2014.

CSL Behring, "Company Core Data Sheet for Beriglobin," Sep. 16, 2015, together with an English translation thereof, 17 pages total.

(56) References Cited

OTHER PUBLICATIONS

Bessen et al., "Passive Acquired Mucosal Immunity to Group A Streptococci by Secretory Immunoglobulin A," Journal of Experimental Medicine, Jun. 1, 1988, vol. 167, No. 6, p. 1945-1950.
English translation of the Japanese Office Action, dated Nov. 1, 2016, for corresponding Japanese Application No. 2014-560392.
Fluckiger et al., "Immunoglobulins Inhibit Adherence and Internalization of *Streptococcus pyogenes* to Human Pharyngeal Cells," Advances in Experimental Medicine and Biology, 1997, vol. 418, p. 909-911.
Fluckiger et al., "Immunoglobulins to Group A *Streptococcal* Surface Molecules Decrease Adherence to and Invasion of Human Pharyngeal Cells," Infection and Immunity, Mar. 1998, vol. 66, No. 3, p. 974-979.
Himi et al., "Immune Barrier Changes in Patients with Head and Neck Cancer," Stomato-pharyngology, 1994, vol. 6, No. 2, p. 71-77, with an English abstract.
Karolewska et al., "Antibacterial potential of saliva in children with leukemia," Oral Surgery, Oral Medicine, Oral Pathology, Oral Radiology, and Endodontics, Jun. 2008, vol. 105, No. 6, p. 739-744.

\* cited by examiner

A

IP-10

B

G-CSF

SEQUENCE LISTING

```
<160> NUMBER OF SEQ ID NOS: 1

<210> SEQ ID NO 1
<211> LENGTH: 764
<212> TYPE: PRT
<213> ORGANISM: Homo sapiens

<400> SEQUENCE: 1

Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60

Ile Thr Leu Ile Ser Ser Glu Gly Tyr Val Ser Ser Lys Tyr Ala Gly
65                  70                  75                  80

Arg Ala Asn Leu Thr Asn Phe Pro Glu Asn Gly Thr Phe Val Val Asn
                85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
    130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
```

-continued

```
            195                 200                 205
Gln Leu Arg Leu Ser Asp Ala Gly Gln Tyr Leu Cys Gln Ala Gly Asp
    210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Asn Thr Leu Gly Lys
        275                 280                 285

Arg Ala Pro Ala Phe Glu Gly Arg Ile Leu Leu Asn Pro Gln Asp Lys
        290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
                325                 330                 335

Ser Pro Ile Gln Ala Trp Gln Leu Phe Val Asn Glu Glu Ser Thr Ile
            340                 345                 350

Pro Arg Ser Pro Thr Val Val Lys Gly Val Ala Gly Gly Ser Val Ala
        355                 360                 365

Val Leu Cys Pro Tyr Asn Arg Lys Glu Ser Lys Ser Ile Lys Tyr Trp
    370                 375                 380

Cys Leu Trp Glu Gly Ala Gln Asn Gly Arg Cys Pro Leu Leu Val Asp
385                 390                 395                 400

Ser Glu Gly Trp Val Lys Ala Gln Tyr Glu Gly Arg Leu Ser Leu Leu
                405                 410                 415

Glu Glu Pro Gly Asn Gly Thr Phe Thr Val Ile Leu Asn Gln Leu Thr
            420                 425                 430

Ser Arg Asp Ala Gly Phe Tyr Trp Cys Leu Thr Asn Gly Asp Thr Leu
        435                 440                 445

Trp Arg Thr Thr Val Glu Ile Lys Ile Ile Glu Gly Glu Pro Asn Leu
    450                 455                 460

Lys Val Pro Gly Asn Val Thr Ala Val Leu Gly Glu Thr Leu Lys Val
465                 470                 475                 480

Pro Cys His Phe Pro Cys Lys Phe Ser Ser Tyr Glu Lys Tyr Trp Cys
                485                 490                 495

Lys Trp Asn Asn Thr Gly Cys Gln Ala Leu Pro Ser Gln Asp Glu Gly
            500                 505                 510

Pro Ser Lys Ala Phe Val Asn Cys Asp Glu Asn Ser Arg Leu Val Ser
        515                 520                 525

Leu Thr Leu Asn Leu Val Thr Arg Ala Asp Glu Gly Trp Tyr Trp Cys
    530                 535                 540

Gly Val Lys Gln Gly His Phe Tyr Gly Glu Thr Ala Ala Val Tyr Val
545                 550                 555                 560

Ala Val Glu Glu Arg Lys Ala Ala Gly Ser Arg Asp Val Ser Leu Ala
                565                 570                 575

Lys Ala Asp Ala Ala Pro Asp Glu Lys Val Leu Asp Ser Gly Phe Arg
            580                 585                 590

Glu Ile Glu Asn Lys Ala Ile Gln Asp Pro Arg Leu Phe Ala Glu Glu
        595                 600                 605

Lys Ala Val Ala Asp Thr Arg Asp Gln Ala Asp Gly Ser Arg Ala Ser
    610                 615                 620
```

```
Val Asp Ser Gly Ser Ser Glu Glu Gln Gly Gly Ser Ser Arg Ala Leu
625                 630                 635                 640

Val Ser Thr Leu Val Pro Leu Gly Leu Val Leu Ala Val Gly Ala Val
                645                 650                 655

Ala Val Gly Val Ala Arg Ala Arg His Arg Lys Asn Val Asp Arg Val
                660                 665                 670

Ser Ile Arg Ser Tyr Arg Thr Asp Ile Ser Met Ser Asp Phe Glu Asn
        675                 680                 685

Ser Arg Glu Phe Gly Ala Asn Asp Asn Met Gly Ala Ser Ser Ile Thr
        690                 695                 700

Gln Glu Thr Ser Leu Gly Gly Lys Glu Glu Phe Val Ala Thr Thr Glu
705                 710                 715                 720

Ser Thr Thr Glu Thr Lys Glu Pro Lys Lys Ala Lys Arg Ser Ser Lys
                725                 730                 735

Glu Glu Ala Glu Met Ala Tyr Lys Asp Phe Leu Leu Gln Ser Ser Thr
                740                 745                 750

Val Ala Ala Glu Ala Gln Asp Gly Pro Gln Glu Ala
                755                 760
```

TREATMENT OF MUCOSITIS WITH IMMUNOGLOBULIN

The invention relates to compositions comprising immunoglobulin for use in the treatment of mucositis by topical application. In particular, the invention relates to compositions comprising J chain-containing IgA and secretory component for the treatment of mucositis.

Cancer patients suffer from various therapy-related sequelae. Mucositis of the alimentary tract is one of the most debilitating adverse effects of chemotherapy and irradiation (Sonis S T (2009) Oral Oncol 45, 1015-20). Pain, mucosal ulcerations, and difficulties in food uptake requiring parenteral nutrition severely affect the patients' comfort and increase the risk of local as well as systemic infection (Elting, L S et al (2003) Cancer 98: 1531-9). In addition, mucositis causes delays in subsequent chemotherapy or radiotherapy cycles. It may necessitate treatment breaks, or dose reduction of chemotherapy, which may have a detrimental effect on overall survival. Mucositis also emerges as an economic issue, as its management requires costly therapies and prolonged hospital stays.

The current standard therapy for mucositis relies predominantly on palliative measures to control pain but do not address the pathomechanisms involved in mucositis.

Understanding the complex pathophysiology of mucositis is crucial to devise preventive and/or therapeutic strategies. The current concept involves five overlapping phases (Sonis S T (1998) Oral Oncol 34: 39-43): (1) Mucositis is initiated during the administration of cytotoxic drugs or irradiation. The damage begins days before the first visible and clinically quantifiable changes occur (e.g. mucosal erythema), possibly caused by DNA damage and/or reactive oxygen species. (2) Damage response pathways and pro-inflammatory cascades are activated. (3) A vicious cycle with amplification of these signaling pathways, e.g. release of TNF-α, activation of NF-κB, and reactive oxygen species, is thought to potentiate cell death and thereby mediate mucosal damage. (4) Visible ulcerations develop, negatively influenced by the presence of a polymicrobial flora on the mucosal surface, potentiating proinflammatory cytokine release (Ratner, A J et al (2005) Proc Natl Acad Sci USA 102: 3429-34). Commensals or facultative pathogens of the oral cavity and the gastrointestinal tract invade ulcers and may cause bacteremia. (5) Regeneration of the mucosal barrier will only occur after toxic stimuli and proinflammatory signals have abated, and the neutrophil count has recovered.

Some of these stages and pathophysiological events can be re-created with studies in vitro and in animal models. Exposure of epithelial cells to radiation or chemicals typically used for chemotherapy (e.g. methotrexate) is an appropriate approach to model the effect and potential collateral damage of anti-cancer therapy on locally present epithelial cells. This corresponds to the early/initiating stages of oral mucositis (stages 1, 2 and 3 as described above). Epithelial cells that might be used to this end include keratinized epithelial cell lines (e.g. Detroit 532) and non-keratinized epithelial cell lines (e.g. H376). Similarly, exposure of epithelial cells to opportunistic pathogens present in the oral microbiota mimics later stages of oral mucositis (stage 3 and 4), especially the perpetuation of inflammation caused by locally present microbes can be studied in such systems. Typical opportunistic pathogens present in the oral microbiome include *Streptococcus* species, particularly *S. mitis* and *S. pneumoniae* and to some extent also *Moraxella* species, including *M. catarrhalis* (The Human Microbiome Project Consortium (2012) Nature 486:207-214) (Dewhirst F E (2010) J. Bacteriol 192:5002-5017).

In addition various in vivo models in hamster, rat and mouse are well established, frequently used and also accepted by Regulatory Authorities. The most commonly used model is based on the Golden Syrian Hamster exposed to radiation or a combination of radiation and chemotherapy; both prophylactic and therapeutic interventions have been described in the model (Watkins B (2010) Oral Dis 16:655-660).

There is a direct correlation between the intensity of the cancer treatment and the risk for the development of mucositis. Increased risk has been observed in patients who developed mucositis in previous treatment cycles. Stress factors such as anxiety also increase the risk. The nature and degree of mucosal microflora and possible modifications of the existing microflora by cancer treatments may also potentiate inflammatory stimuli.

Disruption of pro-inflammatory signals and reduction of microbial load have been identified as potential targets for treatment and/or prophylaxis of mucositis. Only 7 agents tested in more than one comparative, randomized trial were found to have significant effects, but the improvement observed was minor. Oral pastilles containing polymyxine, tobramycin and amphotericin B were found to have a favourable effect (Stokman M A et al (2003) Br J Cancer 88: 1012-6; Wijers O B et al (2001) Int J Radiot Oncol Biol Phys 50: 343-52), although the use of local antimicrobials in mucositis is not routinely recommended (Donelly J P et al (2003) Lancet Infect Dis 3: 405-12). It is currently thought that microorganisms may not cause the initiation of mucositis, but may play a role in subsequent stages. Recently, recombinant keratinocyte growth factor (KFG) was shown to significantly improve mucositis (Blijelevens N & Sonis, S (2007) Ann Oncol 18: 817-26).

Therefore, there is a strong need for effective treatments for mucositis caused by cancer-related treatment regimes. New approaches are urgently needed for the prevention and treatment of mucositis of the alimentary tract, in particular oral mucositis.

SUMMARY OF THE INVENTION

The present inventors have surprisingly found that mucositis of the alimentary tract, in particular oral mucositis, can be treated effectively by topical administration of immunoglobulins, in particular of IgA and/or IgM.

Therefore, one aspect of the invention is a composition comprising immunoglobulin for use in the prevention or treatment of mucositis of the alimentary tract, in particular oral mucositis, by topical administration in a subject.

Preferably, the immunoglobulin comprises IgA and/or IgM, more preferably, the immunoglobulin comprises J chain-containing IgA or J chain-containing IgM or combinations thereof. Preferably, the immunoglobulin is obtainable from blood or a component thereof, such as plasma or plasma fractions. More preferably, the composition of the invention also comprises secretory component. Preferably the secretory component is recombinant secretory component.

In a preferred aspect of the invention, the composition comprises secretory-like IgA. The composition may also comprise secretory-like IgA in combination with another immunoglobulin, preferably in combination with IgM, preferably secretory-like IgM.

A further aspect of the invention is the composition described above, formulated to provide a long contact time with the mucosal area affected (or at risk of getting affected) by mucositis. Preferably, the composition is formulated as a cream, a gel, a syrup, a jelly, a solid form which dissolves near the affected mucosa, or combinations thereof. Another preferred composition is a liquid composition that is formulated to be suitable for retaining in the mouth for a few minutes before swallowing or disgorging. Preferably, the liquid formulation comprises flavoring substances so that the taste is comfortable. Such substances may confer a taste of fruit such as strawberry, apple, peach, blueberry; a taste of caramel, chocolate; savory tastes may also be used, such as cheese or tomato. The composition may also comprise other suitable excipients, for example stabilizing agents that enhance the stability of the immunoglobulins.

Yet another aspect of the invention is the composition described above, wherein the topical application to the mucosa reduces adherence and/or invasion of a microorganism or microorganisms, such as bacteria or fungi. The microorganism may be part of the microflora on the mucosal surface.

A further aspect of the invention is the composition described above, wherein the topical application to the mucosa promotes mucosal wound healing. Preferably, the composition of the invention stimulates epithelial cells to secrete growth factors, e.g. keratinocyte growth factor.

Yet a further aspect of the invention is the composition of the invention, wherein the topical application to the mucosa exerts an anti-inflammatory effect. The anti-inflammatory effect may be
 (a) inhibition of pro-inflammatory cytokine expression; and/or
 (b) stimulation of the expression of anti-inflammatory cytokines.

Another aspect of the invention is the composition described above, wherein the subject is at risk of developing mucositis of the alimentary tract such as a cancer patient undergoing or about to undergo chemotherapy and/or radiotherapy. In particular, a subject at risk of developing mucositis is a cancer patient who developed mucositis as a result of a previous chemotherapy and/or radiotherapy treatment. The previous chemotherapy and/or radiotherapy treatment may be an earlier cycle of treatment in a series of treatment cycles, or a treatment part of a series of treatment cycles in a patient who was in remission after receiving chemotherapy and/or radiotherapy, but where the cancer has reappeared and another series of chemotherapy and/or radiotherapy is indicated. Preferably, the administration of the composition commences when the patient's neutrophil count starts declining. Preferably, the treatment is maintained for the period where the patient's neutrophil count is below normal.

The composition of the invention is administered to the subject up to 6 times per day, preferably up to 5 times per day, more preferably up to 4 times per day, even more preferably up to 3 times per day, most preferably 2 times per day or even less frequently.

In another aspect of the invention, the composition comprises an additional effective agent for the treatment of mucositis, such as a growth factor or an antiseptic agent. Also included in the invention is a product comprising the composition of the invention and a second active agent as a combined preparation for simultaneous, separate or sequential use in the treatment of mucositis of the alimentary tract. Such a second active agent may be, for example, an agent promoting wound healing, such as a growth factor, an antimicrobial agent such as an antiseptic agent, e.g. an antiseptic mouthwash, or an anti-inflammatory agent.

DETAILED DESCRIPTION OF THE INVENTION

As mentioned above, mucositis in cancer patients, in particular oral mucositis, is still regarded as a major medical problem, and there is a need for an effective treatment. The present inventors have now surprisingly found that mucositis of the alimentary tract, in particular oral mucositis, can be treated effectively by topical administration of immunoglobulins, in particular of IgA and/or IgM.

Therefore, one aspect of the invention is a composition comprising immunoglobulin for use in the prevention or treatment of mucositis of the alimentary tract, in particular oral mucositis, by topical administration in a subject. Preferably the immunoglobulin is human immunoglobulin.

Preferably, the immunoglobulin comprises IgA or IgM or a combination thereof, more preferably, the immunoglobulin comprises J chain-containing IgA or J chain-containing IgM or a combination thereof. Preferably, the immunoglobulin is obtainable from blood or a component thereof, such as plasma, cryo-poor plasma, or plasma fractions. More preferably, the immunoglobulins are purified from side fractions that are obtained during the processing of plasma for the purification of other plasma proteins, for example immunoglobulin G. Preferably the immunoglobulin is not obtained from milk or colostrum. Preferably, the immunoglobulin is not modified after purification by altering the glycosylation in vitro, e.g. by enzymatic addition or removal of sugar residues, e.g. mannose or sialic acid or galactose. Preferably, the immunoglobulin is not a pure anti-TNF antibody or immunoglobulin enriched for anti-TNF or purified from a human or animal donor immunized with TNF-α.

In another aspect of the invention, the composition also comprises secretory component. Preferably the secretory component is recombinant secretory component, preferably secretory component produced in a mammalian cell line.

The term "secretory component" as used herein refers to a protein that specifically binds to J-chain-containing immunoglobulin, and is related to or derivable from or identical to an extracellular portion of the polymeric immunoglobulin receptor (pIgR), preferably a mammalian pIgR, more preferably a primate pIgR, most preferably a human pIgR. Preferably, the secretory component confers increased stability to the J-chain containing immunoglobulin. Secretory component in its traditional, narrow meaning (referred to as "natural secretory component" herein) is the extracellular portion of the polymeric immunoglobulin receptor (pIgR), which usually gets associated during secretion with dimeric or polymeric IgA or pentameric IgM comprising a J chain. J chain-containing IgA/IgM binds to the polymeric immunoglobulin receptor at the basolateral surface of epithelial cells and is taken up into the cell by transcytosis. This receptor complex then transits through the cellular compartments before being transported to the luminal surface of the epithelial cells. The transcytosed IgA/IgM-pIgR complex is then released through proteolysis, and part of the polymeric immunoglobulin receptor (pIgR), referred to as the natural secretory component, stays associated with the J chain-containing IgA/IgM, releasing secretory IgA/IgM. However, there is evidence that reverse transcytosis of IgA, i.e. from the luminal surface to the basolateral surface, can also take place.

The human pIgR is cloned and sequenced, its sequence is available as SwissProt entry P01833, and shown in Seq ID NO: 1. Human pIgR is a glycoprotein with 764 amino acid residues, containing a signal peptide (residues 1 to 18), an extracellular part (residues 19 to 638), a transmembrane region (residues 639 to 661), and a cytoplasmic region (residues 662 to 764). Residues 19 to 603 are thought to associate with J chain-containing IgA or J chain-containing IgM as described above, and this part of this glycoprotein is usually referred to as the secretory component ("natural secretory component").

The secretory component used in the composition of the invention can comprise any extracellular pIgR sequence that is capable of associating with J chain-containing IgA. For example, secretory component may comprise extracellular domains of pIgR from mammalian sources, e.g. from primates, cattle, horses, cats, dogs, rabbits, guinea pigs, rats or mice, or variants thereof. Functional hybrids of the extracellular domains from several mammalian species or variants thereof are also contemplated for use in the invention, e.g. prepared by fusing the immunoglobulin-like domains from different species into a secretory component-like protein. A functional secretory component may also be formed by fusing a selection of immunoglobulin-like domains normally present, e.g. rabbit secretory component is functional being composed of only domains 1, 4 and 5. Preferably, however, the human secretory component or functional variants thereof is used.

Therefore the secretory component used in the composition of the invention preferably comprises residues 19 to 603 of SEQ ID NO: 1 or functional variants thereof. Functional variants may include deletions, insertions, and/or substitutions, preferably substitutions are conservative substitutions, e.g. a basic amino acid residue is substituted for another basic amino acid, a hydrophobic amino acid is substituted for another hydrophobic amino acid, etc. The variant secretory component is at least 50% identical in sequence to residues 19 to 603 of SEQ ID NO: 1, preferably at least 55%, 60%, 65%, 70%, 75%, 80%, more preferably at least 85% or even 90%, even more preferably at least 92%, 94%, 95%, 97%, 98%, or even 99% identical to residues 19 to 603 of SEQ ID NO: 1. Most preferably, the secretory component comprises or even consists of residues 19 to 603 of SEQ ID NO: 1.

The skilled person is well aware how to produce the secretory component by recombinant techniques. An example of expression of human secretory component in CHO cells has been described by Phalipon et al (Phalipon A et al (2002) Immunity 17:107-115), but the invention is not limited to secretory component produced by this system. For example, the desired cDNA sequence can be produced synthetically or cloned via RT-PCR, using RNA isolated from cells or tissue expressing pIgR as template. The cDNA can then be inserted into a mammalian expression vector such as pcDNA3—many alternative expression vectors are available and are well known to the skilled person. The recombinant expression vector will then be introduced into a suitable host cell line, such as CHO, Cos, HEK293, or BHK. Other cell lines are available and can also be used. Methods for introducing such vectors into a cell line include lipofection, electroporation and other techniques well known to the skilled person. Usually cells harboring the expression vector and expressing the protein of interest are then selected and cloned. Viral expression systems can also be used, for example, vaccinia virus can be used to express proteins at high levels in mammalian cells, baculovirus expression systems can be used to express proteins at high levels in insect cells. Yeast or bacterial expression systems can also be envisaged, and such expression systems are known to the skilled person. Plant expression systems can also be used and are known to the skilled person.

The secretory component or variant thereof used in the composition of the invention may also comprise a tag, such as a hexa-Histidine tag, which can aid in the purification of the resulting protein. If such a tag is attached via a cleavable linker, the tag may be cleaved off prior to use in the invention. Similarly, the secretory component may be produced as a fusion protein. Again, a cleavable linker may be used so that the fusion partner may be cleaved off the secretory component prior to use in the invention.

The skilled person can then purify the expressed protein with standard methods.

The secretory component may also be obtained from a natural source, preferably from milk, saliva or mucus. Preferably the secretory component is of human origin, but secretory component from other species can also be used in the invention.

The molar ratio between secretory component and J chain within the composition is between 1:10 and 10:1, preferably between 1:5 and 5:1, more preferably between 1:2 and 2:1.

The amount of secretory component used in the composition may be 1 part (by weight) of secretory component to at least 50 parts (by weight) of protein in the composition, preferably 1 part to at least 40, 30, 20, 15, 10, most preferably 1 part of secretory component to at least 5 parts of protein in the composition.

In a preferred aspect of the invention, the composition comprises secretory-like IgA. The composition may also comprise secretory-like IgA in combination with another immunoglobulin, preferably in combination with IgM, preferably secretory-like IgM. In another preferred aspect of the invention, the composition may also comprise secretory-like IgM alone or in combination with other immunoglobulins.

A further aspect of the invention is the composition described above, formulated to provide a long contact time with the mucosal area affected (or at risk of getting affected) by mucositis. "Contact time" refers to the amount of time the composition or parts thereof remain active on the affected mucosal surface or the mucosal surface at risk. Preferably, the contact time is longer than a few minutes, more preferably hours, even more preferably days, most preferably long enough to exert a biological effect which is prevention or treatment of mucositis. Preferably, the composition is formulated as a cream, a gel, a syrup, a jelly, a solid form which dissolves near the affected mucosa, or combinations thereof. The composition may also be formulated as a tablet, comprising one or more suitable excipients such as sucrose, lactose, maltodextrin, starch (e.g. from corn), cellulose derivatives, e.g. hydroxyethyl cellulose, methyl cellulose, or acrylate, methacrylic acid resins, oil (e.g., olive oil), beeswax or similar agents, alone or in combination. It may also comprise effervescent components. A gel may be formed, for example, using porcine gelatin or starch-based materials, propylene glycol, PEG 40, potassium sorbate, sodium benzoate, benzalkonium chloride, saccharose, sodium hyaluronate, hydroxethyl cellulose or similar agents. A syrup may be formed by adding one or more of sugars, sugar polyols like glycerol or sorbitol, acids to prevent recrystallization of sugar, buffering agents, chelating agents, flavouring agents and flavour enhancers, colouring agents. A jelly may be formed, for example, by using gelatin, e.g. porcine gelatin.

Alternatively, a liquid composition is used, formulated to be suitable for retaining in the mouth for a few minutes before swallowing or disgorging. Preferably, the liquid formulation comprises flavouring substances so that the taste is comfortable. Such substances may confer a taste of fruit such as strawberry, apple, peach, blueberry; a taste of caramel, chocolate, nuts or similar; savory tastes may also be used, such as cheese or tomato. The composition may also comprise other suitable excipients, for example stabilizing agents that enhance the stability of the immunoglobulins, colouring agents, buffer substances, etc.

The composition may be directly applied in the mouth, if the subject is at risk of developing oral mucositis, it may also be taken orally, in a formulation that is designed to release it in other parts of the alimentary tract. It may also be delivered anally, and may be supplied in a suitable formulation for this form of delivery. It may be delivered in a formulation that controls its release in certain areas of the alimentary tract. The skilled person will be able to formulate the composition of the invention to achieve the desired contact time with the mucosa as desired.

Yet another aspect of the invention is the composition described above, wherein the topical application to the mucosa reduces adherence and/or invasion of a microorganism or microorganisms, such as bacteria or fungi. The microorganism may be part of the microflora on the mucosal surface, e.g. the oral microbiota or the intestinal microbiota. Preferably, the composition comprises immunoglobulin that binds to the microorganism and/or toxin produced by the microorganism. Preferably, the adherence and/or invasion by microorganisms to the intact or injured mucosal surface is reduced by at least 25%, preferably by at least 30%, 35%, 40%, 45%, more preferably by at least 50%, ideally to an even greater extent such as at least 60%, 70%, 80%, 90%, in order, for example, to prevent the activation of intracellular pro-inflammatory downstream cascades, which result upon binding of specific microbial surface components (e.g., PAMP, pathogen associated molecular patterns) with surface exposed or intracellular PRR (pattern recognition receptors, e.g., Toll-like receptors).

A further aspect of the invention is the composition described above, wherein the topical application to the mucosa promotes mucosal wound healing. Preferably, the composition of the invention stimulates epithelial cells to secrete one or more growth factors, e.g. keratinocyte growth factor (KGF), or other wound healing promoting factors such as epithelial growth factor (EGF), fibroblast growth factors (e.g. bFGF), granulocyte-macrophage colony-stimulating factor (GM-CSF), transforming growth factors (e.g. TGF-α or β), platelet-derived growth factor (PDGF) and vascular endothelial growth factor (VEGF). The composition may thus stimulate epithelial cells and fibroblasts of the lamina propria to secrete components of extracellular matrix, such as collagen, laminin or fibronectin and to promote angiogenesis.

Preferably, the stimulation to secrete a growth factor is biologically significant, e.g. the secretion of a growth factor is stimulated to such an extent that a significant effect on target cells is achieved.

Yet a further aspect of the invention is the composition of the invention, wherein the topical application to the mucosa exerts an anti-inflammatory effect. The anti-inflammatory effect of the composition of the invention can be characterized further into (a) inhibition of pro-inflammatory cytokine expression; and/or (b) stimulation of the expression of anti-inflammatory cytokines.

Preferably, the expression of one or more key pro-inflammatory cytokines in the mucosa is reduced by the composition of the invention, more preferably, the expression of two or more key pro-inflammatory cytokines is reduced, even more preferably, the expression of three or more pro-inflammatory cytokines is reduced. Preferably, the pro-inflammatory cytokine is selected from IL-1, IL-6, IL-8, IL-17, IFN-γ, TNF-α, MCP-1, IP10. Preferably, the reduction of expression is a reduction of at least 25%, preferably by at least 30%, 35%, 40%, 45%, more preferably by at least 50%, ideally to an even greater extent such as at least 60%, 70%, 80%, 90% or even higher.

Preferably, the expression of one or more key anti-inflammatory cytokines is stimulated by the composition of the invention, more preferably, the expression of two or more of anti-inflammatory cytokines is stimulated, even more preferably, the expression of three or more anti-inflammatory cytokines is stimulated. Preferably, the anti-inflammatory cytokine is selected from IL-1Ra, IL-4, IL-10, IL-11, IL-13, TGF-3. Preferably, the stimulation of expression is a stimulation by at least 2-fold, more preferably by at least 5, 10, 20, 50-fold even more preferably by at least 100-fold, most preferably by more than 500-fold or even more.

More preferably, both a reduction of expression of pro-inflammatory cytokines and a stimulation of expression of anti-inflammatory cytokines is provided by the composition of the invention.

Another aspect of the invention is the composition described above, wherein the subject at risk of developing mucositis of the alimentary tract is a cancer patient undergoing or about to undergo chemotherapy and/or radiotherapy. In particular, a subject at risk of developing mucositis is a cancer patient who developed mucositis as a result of a previous chemotherapy and/or radiotherapy treatment. The previous chemotherapy and/or radiotherapy treatment may be an earlier cycle of treatment in a series of treatment cycles, or a treatment part of a series of treatment cycles in a patient who was in remission after receiving chemotherapy and/or radiotherapy, but where the cancer has reappeared and another series of chemotherapy and/or radiotherapy is indicated.

The composition of the invention may be given prophylactically or as treatment for active, existing mucositis. Preferably, treatment is initiated prior to symptoms of mucositis occurring. The treatment may be initiated prior to, at the same time as, or after commencing chemotherapy and/or radiotherapy. Preferably, in patients receiving chemotherapy the administration of the composition commences when the patients becomes neutropenic (i.e., absolute neutrophil count (ANC)<$0.5 \times 10^9$/L) and, therefore, at risk of developing mucositis. Preferably, the treatment is continued throughout the neutropenic period until the ANC begins to recover or reaches $0.5 \times 10^9$/L and mucositis has resolved clinically. Chemotherapeutic agents frequently inducing mucositis include, among others, methothrexate, anthracyclines, 5-fluorouracil, and myeloablative chemotherapy regimens. Preferably, in patients receiving local radiation therapy, the composition is administered during the entire duration of therapy and until mucositis has resolved.

The composition of the invention is administered to the subject up to 6 times per day, preferably up to 5 times per day, more preferably up to 4 times per day, even more preferably up to 3 times per day, most preferably 2 times per day or even less frequently.

In another aspect of the invention, the composition comprises an additional effective agent for the treatment of mucositis, such as a growth factor or an antiseptic agent. Also included in the invention is a product comprising the composition of the invention and a second active agent as a combined preparation for simultaneous, separate or sequential use in the treatment of mucositis of the alimentary tract. Such a second active agent may be, for example, an agent promoting wound healing, such as a growth factor, an antimicrobial agent such as an antiseptic agent, e.g. an antiseptic mouthwash, or an anti-inflammatory agent.

The invention will now be illustrated in the following non-limiting examples, with reference to the following figures:

LIST OF FIGURES

FIG. 1. Immunoblot analysis (10% sodium dodecyl sulfate-polyacrylamide gel electrophoresis) with 0.5 µg/ml of protein per mm of gel slot with subsequent Western transfer and detection of OMP using mAb1707 (specific for both trimeric and monomeric UspA1 and UspA2) [panel A], mAb24B5 (specific for monomeric UspA1) [panel B], and mAb10F3 (specific for CopB) [panel C]. A HRP-conjugated secondary goat anti-mouse IgG antibody was used for primary antibody detection.

Figure 2:
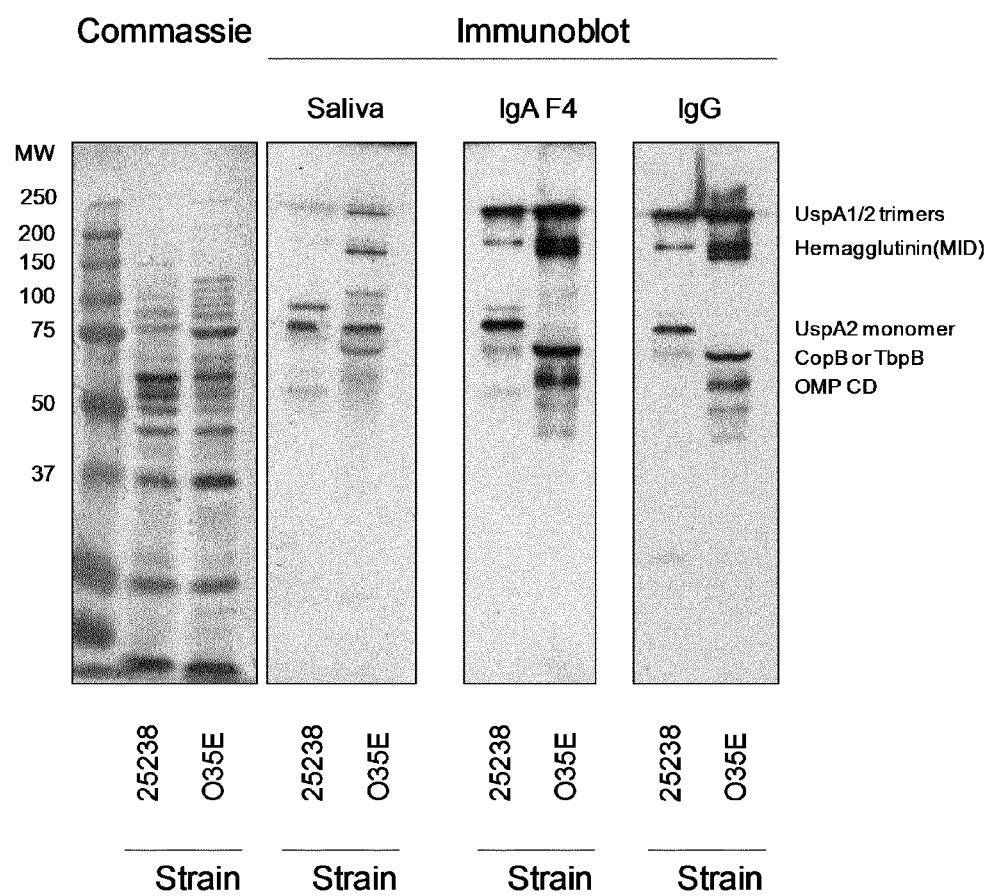

FIG. 2. Immunoblot analysis (10% sodium dodecyl sulfate-polyacrylamide gel electrophoresis) with 0.4 µg/ml of protein per mm of gel slot with subsequent Western transfer and detection of antibody binding using as source of primary antibody human pooled saliva (0.3 g/l) [panel A], plasma IgA F4 [panel B] or pooled plasma IgG (Privigen®) [panel C], and appropriate HRP-conjugated secondary antibodies for visualization using chemiluminescence.

Figure 3:
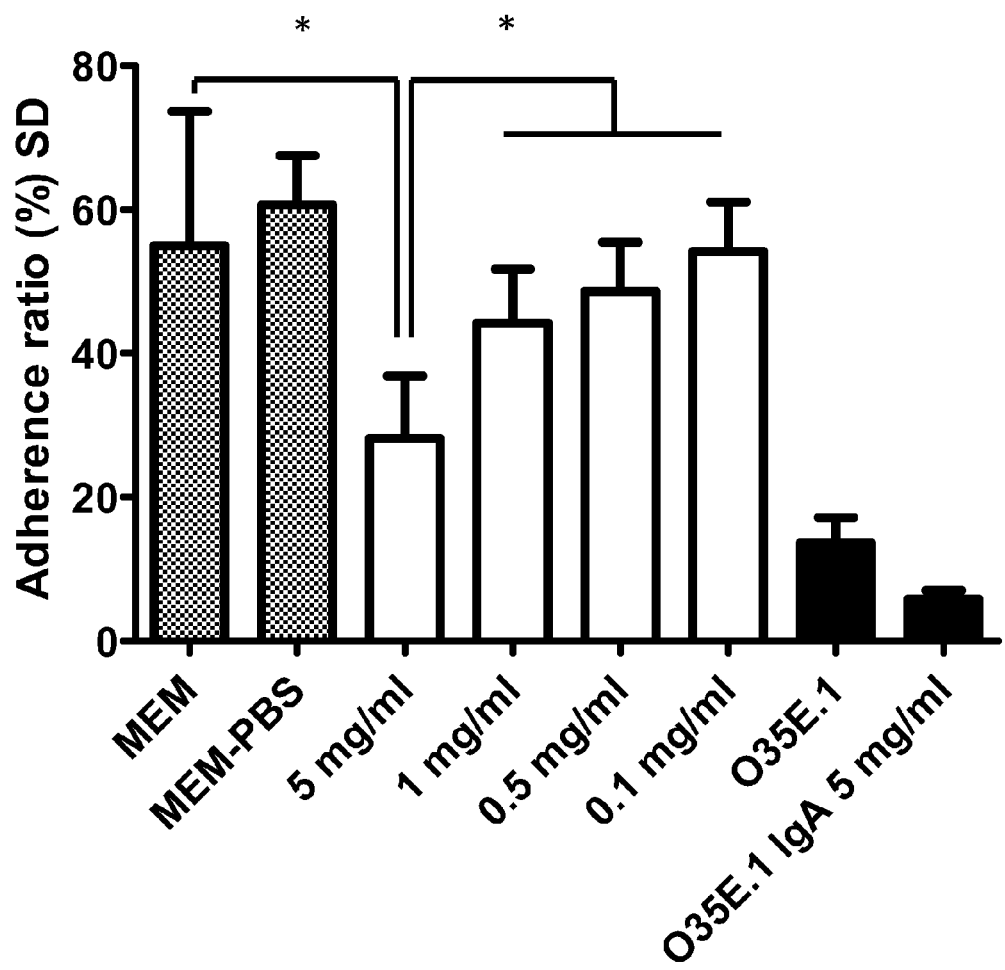

FIG. 3. Adherence inhibition assay using IgA F4. MEM and MEM-PBS were used as negative controls. O35E.1 and O35.1 supplemented with 5 mg/ml of IgA F4 were used as positive controls. The overall p value (one-way ANOVA) was <0.0001; * indicates a level of significance<0.05.

Figure 4:
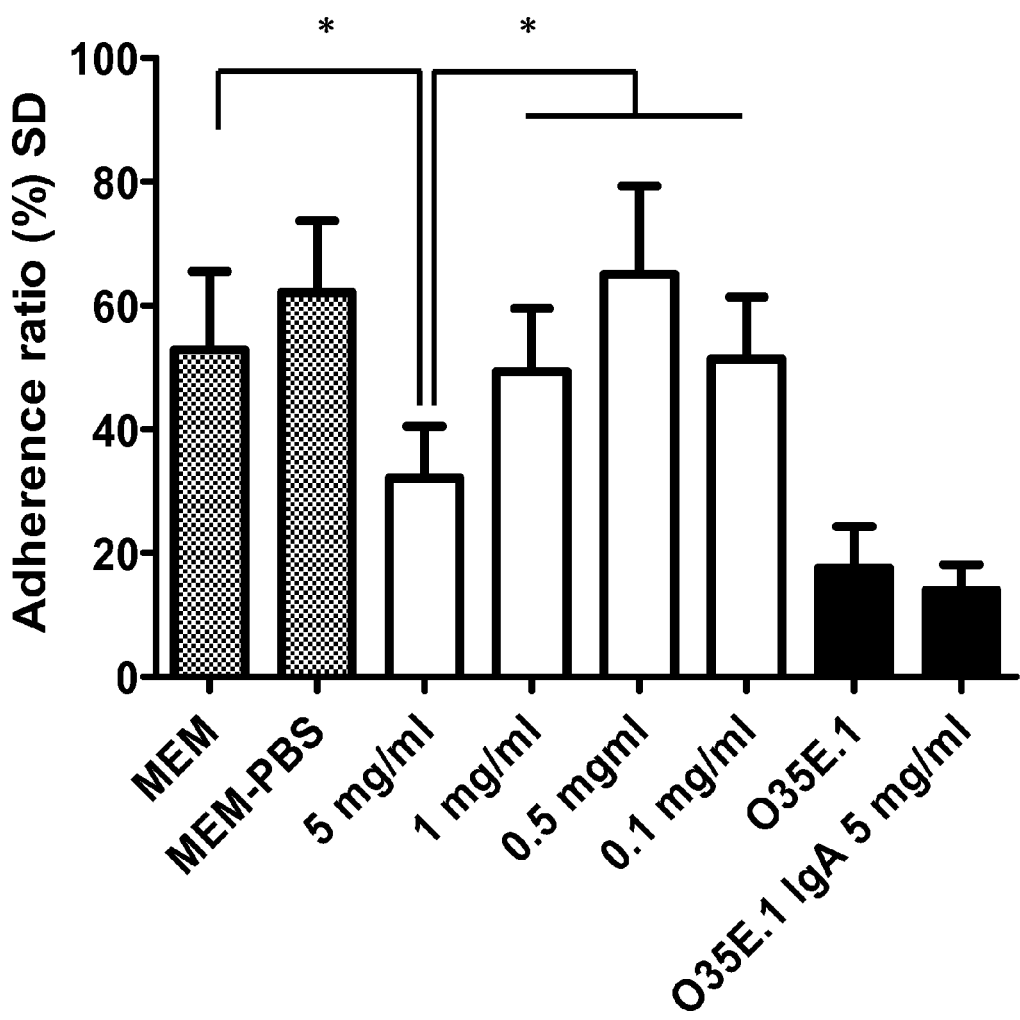

FIG. 4. Adherence inhibition assay using IgA F5A. MEM and MEM-PBS were used as negative controls. O35E.1 and O35.1 supplemented with 5 mg/ml of IgA F5A were used as positive controls. The overall p value (one-way ANOVA) was <0.001; * indicates a level of significance<0.05.

Figure 5:
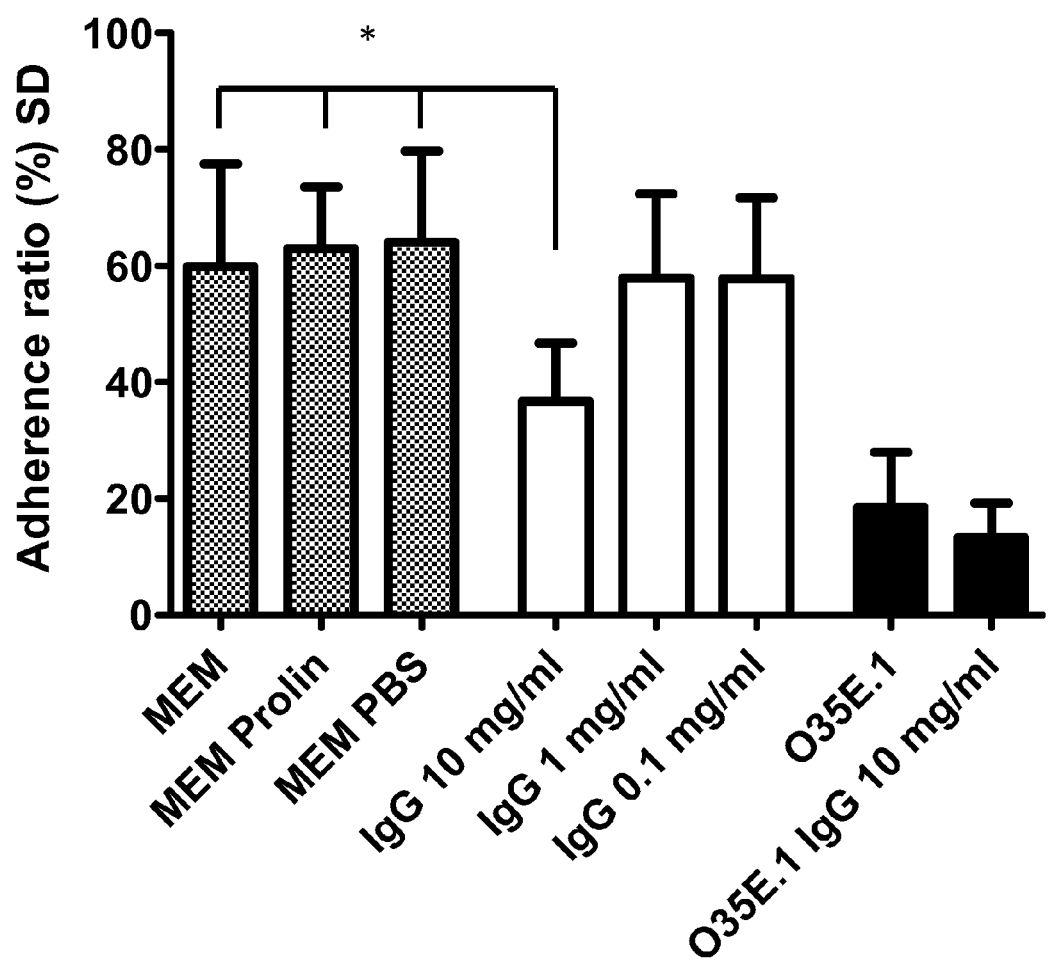

FIG. 5. Adherence inhibition assay using IgG (Privigen®). MEM, MEM-proline, and MEM-PBS were used as negative controls. O35E.1 and O35E.1 supplemented with 10 mg/ml of IgG were used as positive controls. The overall p value (one-way ANOVA) was 0.009; none of the inter-column differences reached statistical significance.

Figure 6:
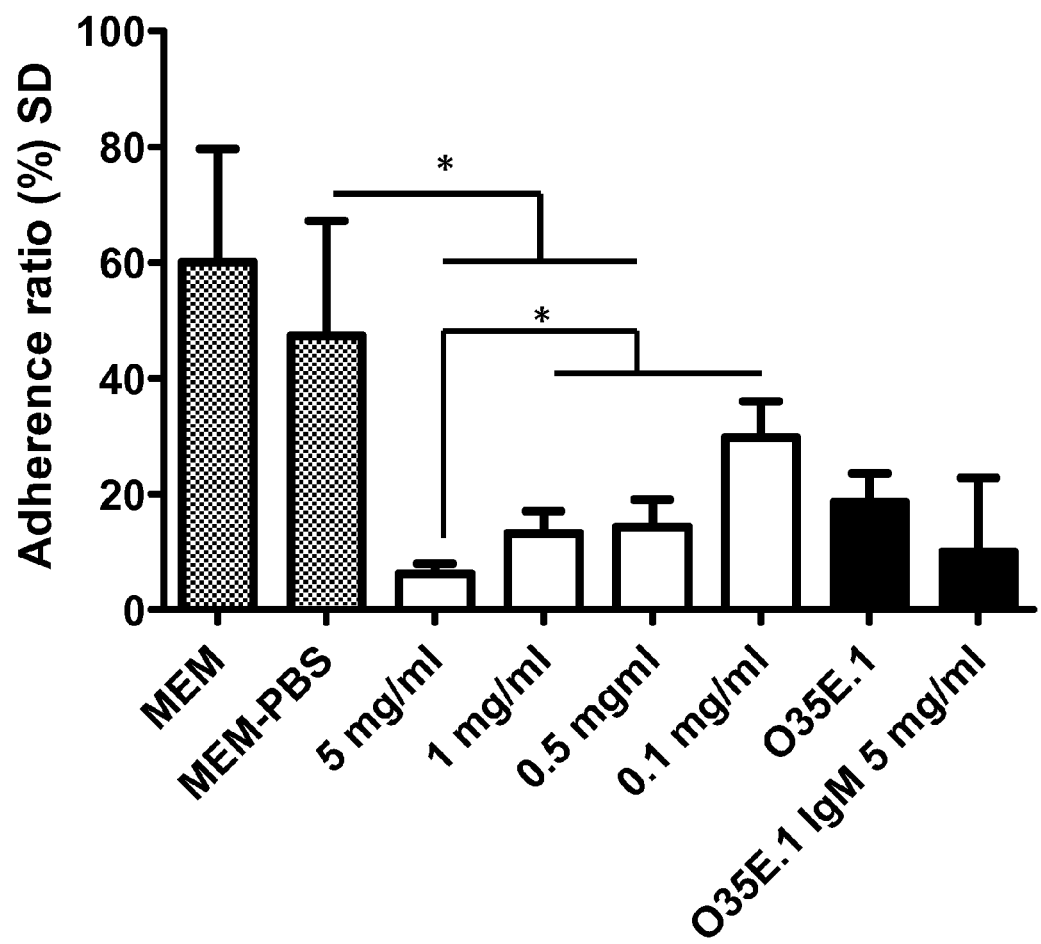

FIG. 6. Adherence inhibition assay using IgM F5A. MEM and MEM-PBS were used as negative controls. O35E.1 and O35.1 supplemented with 5 mg/ml of IgM F5A were used as positive control. The overall p value (one-way ANOVA) was <0.001; * indicates a level of significance<0.05.

Figure 7:
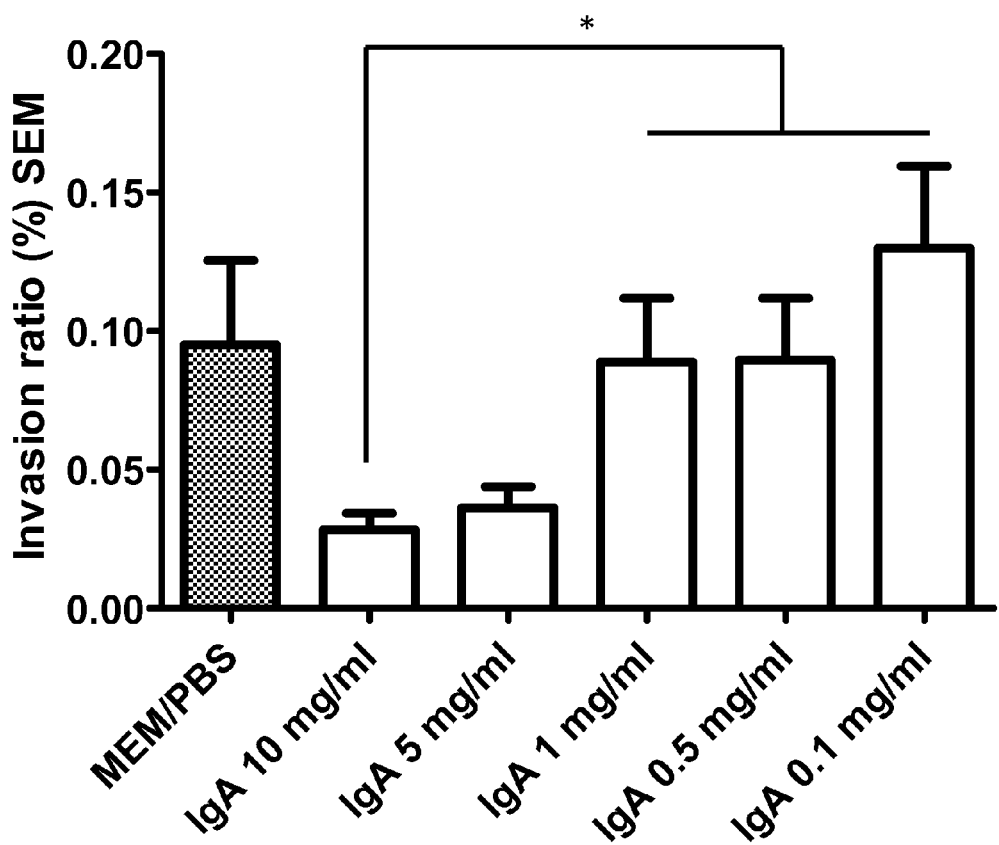

FIG. 7. M. catarrhalis invasion assay demonstrating that IgA F4 at a concentration of 10 mg/ml significantly inhibited the penetration of bacteria into epithelial cells. The overall p value (one-way ANOVA) was 0.014; * indicates a level of significance<0.05. Reliable controls showing complete inhibition of cellular invasion were not available.

Figure 8:
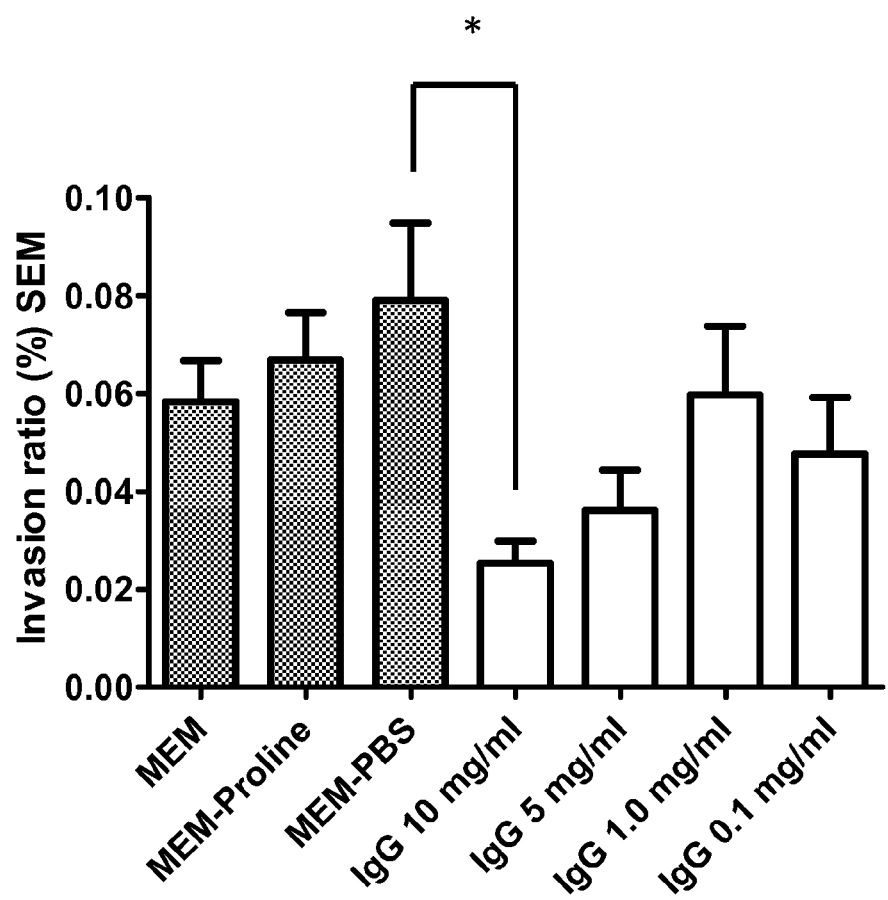

FIG. 8. M. catarrhalis invasion assay demonstrating that pooled human plasma IgG (Privigen®) at a concentration of 10 mg/ml significantly inhibited the penetration of bacteria into epithelial cells. The overall p value (one-way ANOVA) was 0.015; * indicates a level of significance<0.05. Reliable controls showing complete inhibition of cellular invasion were not available.

Figure 9:
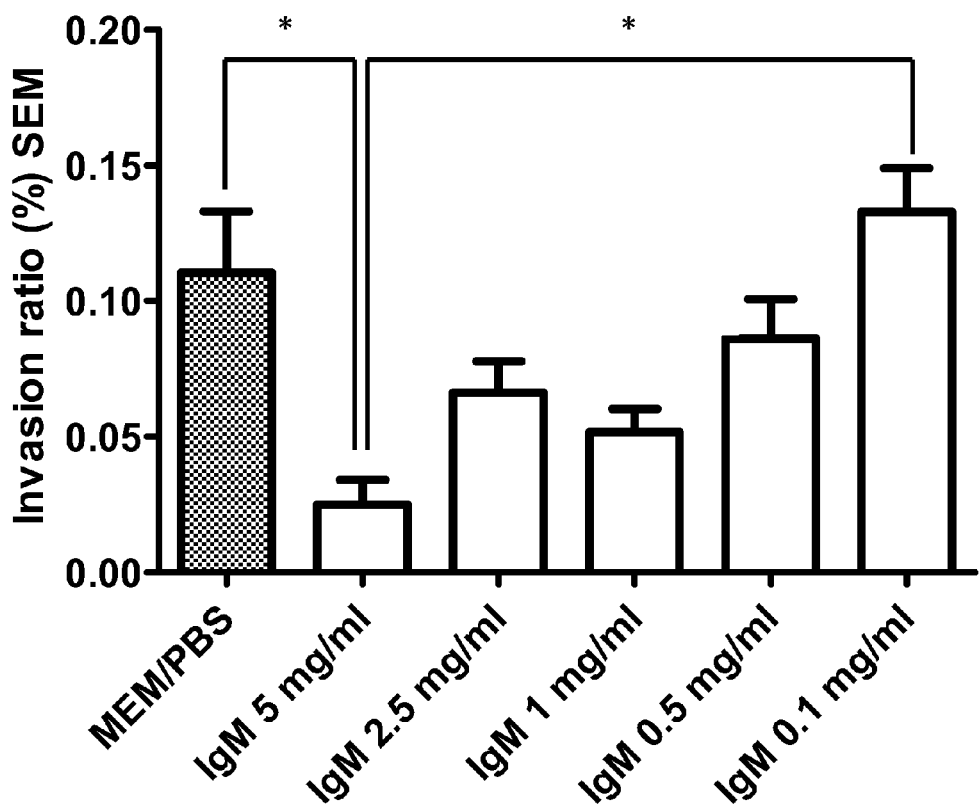

FIG. 9. M. catarrhalis invasion assay demonstrating that IgM F5A at a concentration of 5 and 2.5 mg/ml significantly inhibited the penetration of bacteria into epithelial cells. The overall p value (one-way ANOVA) was <0.0001; * indicates a level of significance<0.05. Reliable controls showing complete inhibition of cellular invasion were not available.

Figure 10:
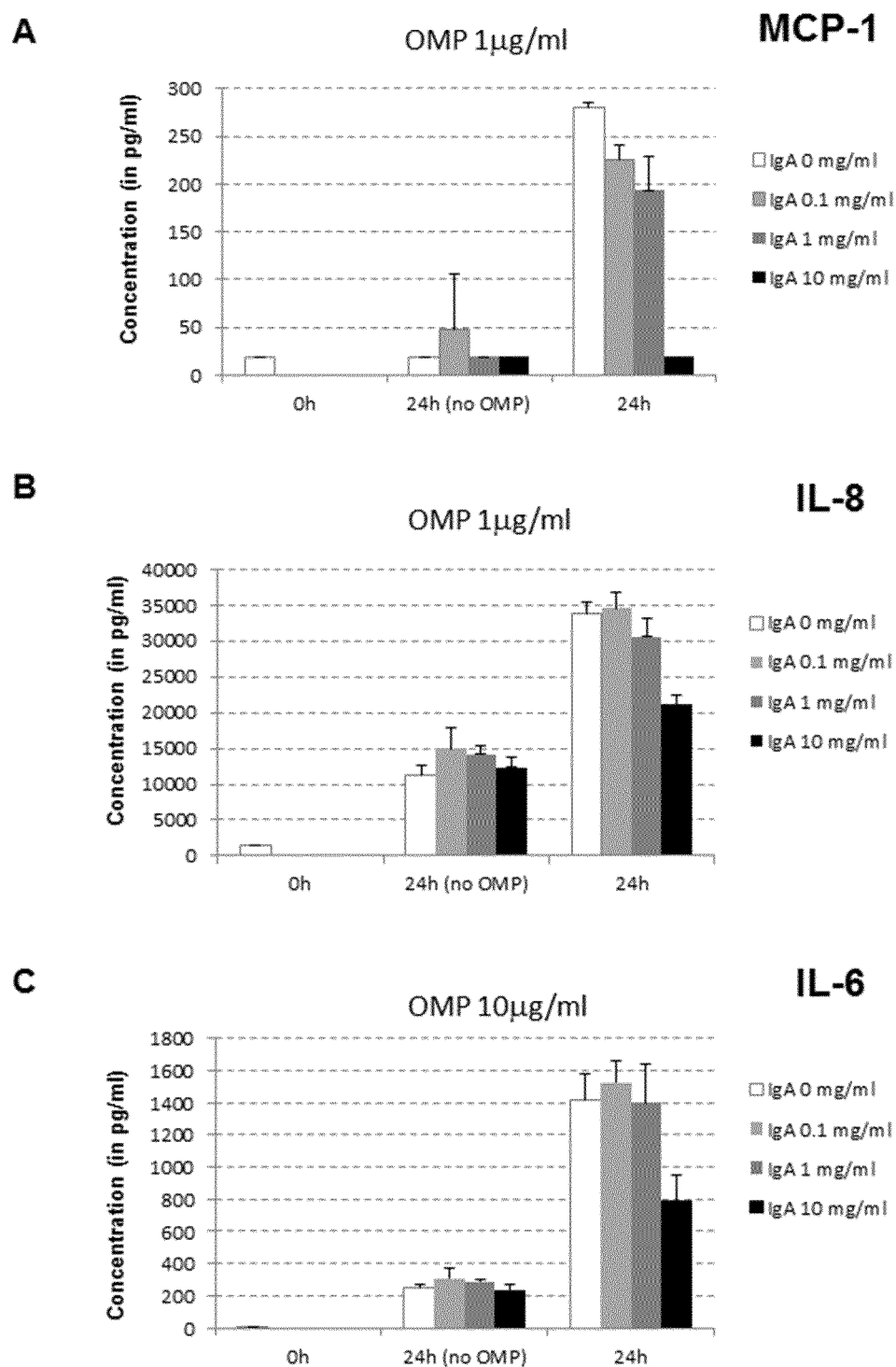

FIG. 10. Anti-inflammatory activity of IgA F4 was assessed using Detroit 562 cells stimulated with M. catarrhalis outer membrane protein (OMP). Increasing concentrations of IgA were applied on cells at the time of OMP stimulation. Secretions of MCP-1 (A), IL-8 (B) and IL-6 (C) by Detroit 562 cells were measured at the start of the stimulation (t=0) and 24 h later (t=24) using a multiplex suspension array (Luminex technology). Negative controls are samples in which no OMP was added.

Figure 11:
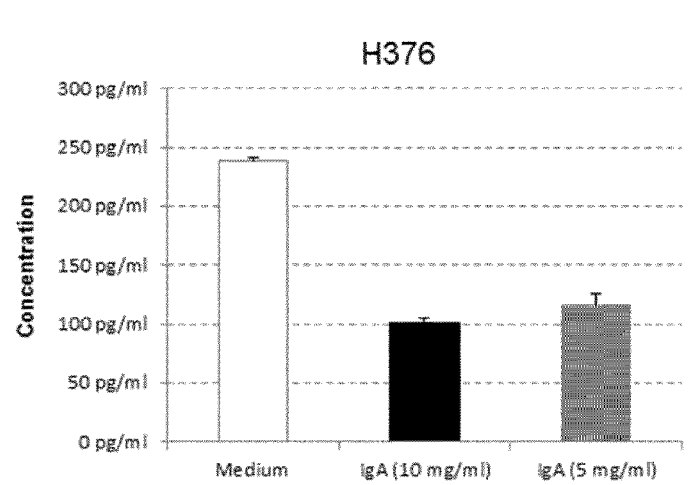
Figure 11:
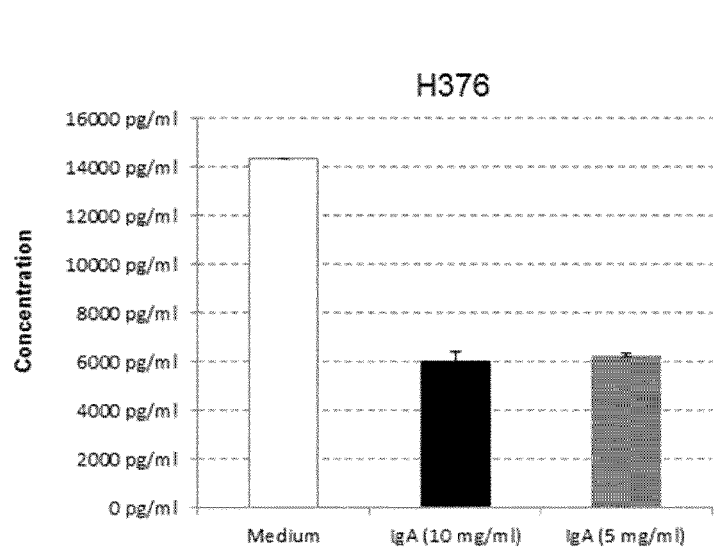
Figure 11:
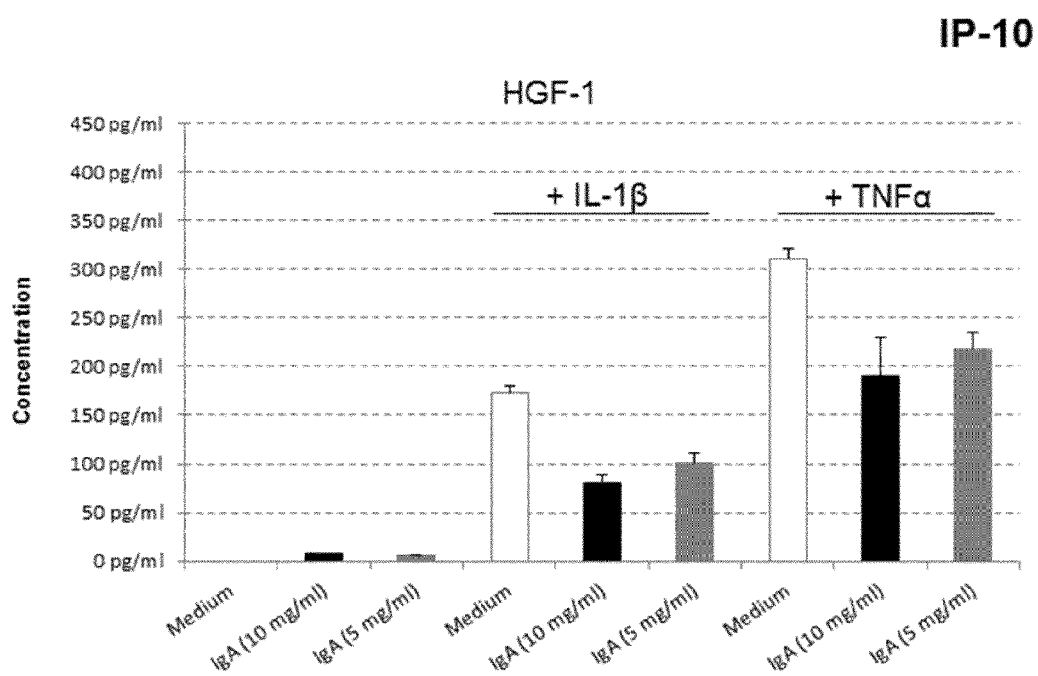

FIG. 11. Anti-inflammatory activity of IgA F4 was assessed using H376 and HGF-1 cells. Increasing concentrations of IgA were applied on resting H376 and HGF-1 cells or at the time of stimulation (HGF-1 cells). Secretions of IP-10 (A) and G-CSF (B) by H376 and IP-10 by HGF-1 (C) cells were measured 24 h after stimulation using a multiplex suspension array (Luminex technology).

Figure 12:
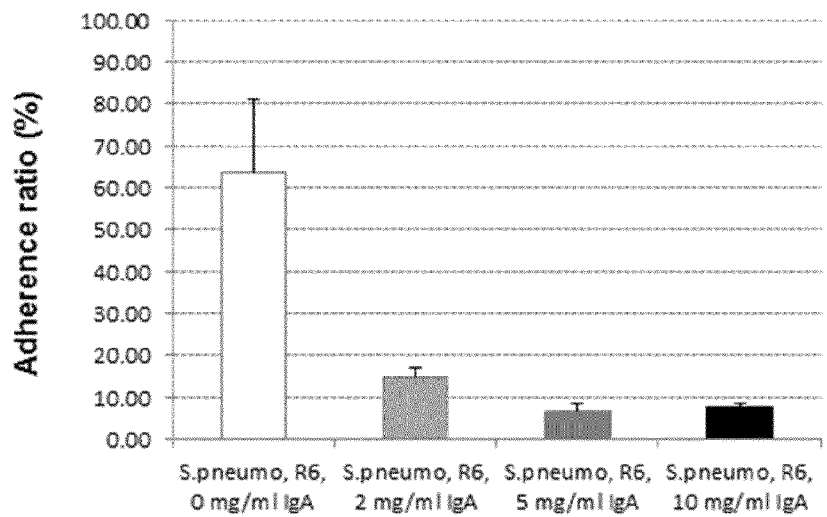
Figure 12:
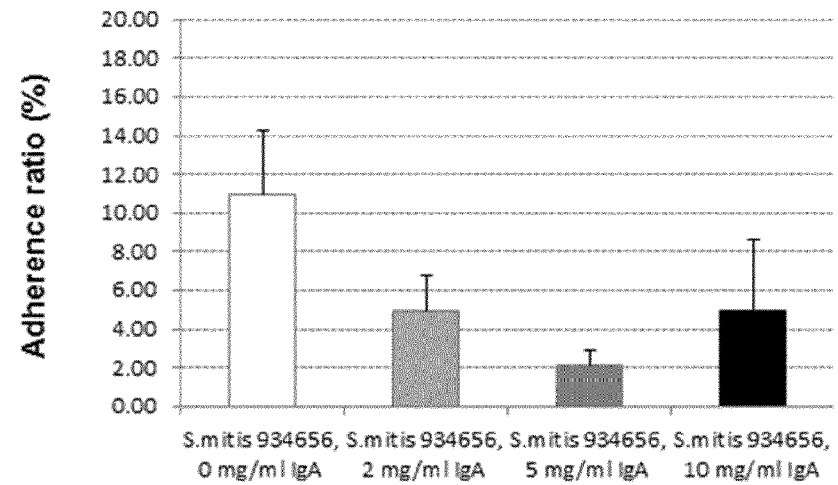

FIG. 12. Adherence inhibition assay using IgA F4. IgA F4 interferes with the adherence capacities of S. pneumoniae R6 (A) and S. mitis (B) to H376 cells.

Figure 13:
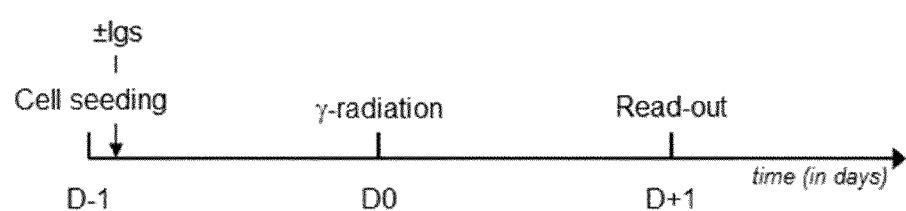
Figure 13:
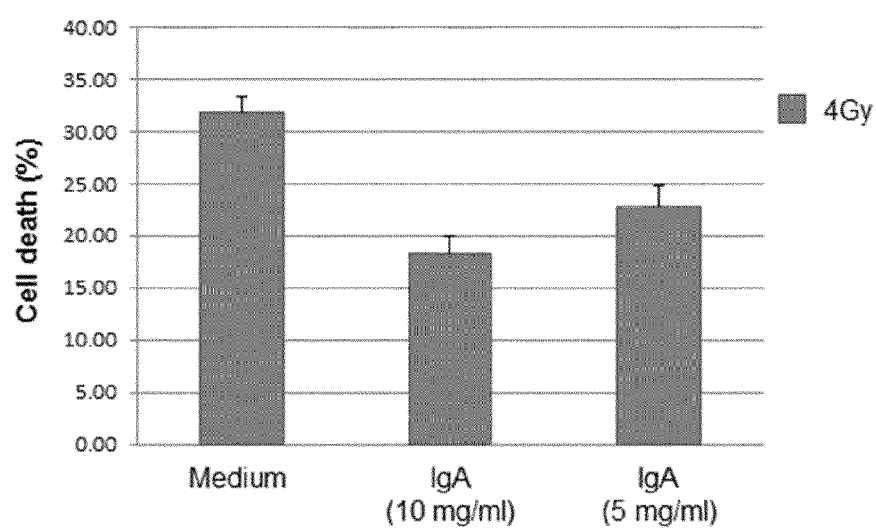

FIG. 13. Cell cytotoxicity assay using IgA F4. Dose effect reduction of IgA F4 on γ-irradiation-induced cell death of H376 cells. (A) The experiment was performed as depicted in the timeline. (B) 24 h after irradiation, cell death was measured using the CytoTox-Glo™ Cytotoxicity Assay (Promega). Numbers correspond to specific cell death related to the total cytotoxicity which was measured in H376 cell samples treated with digitonin.

Figure 14:
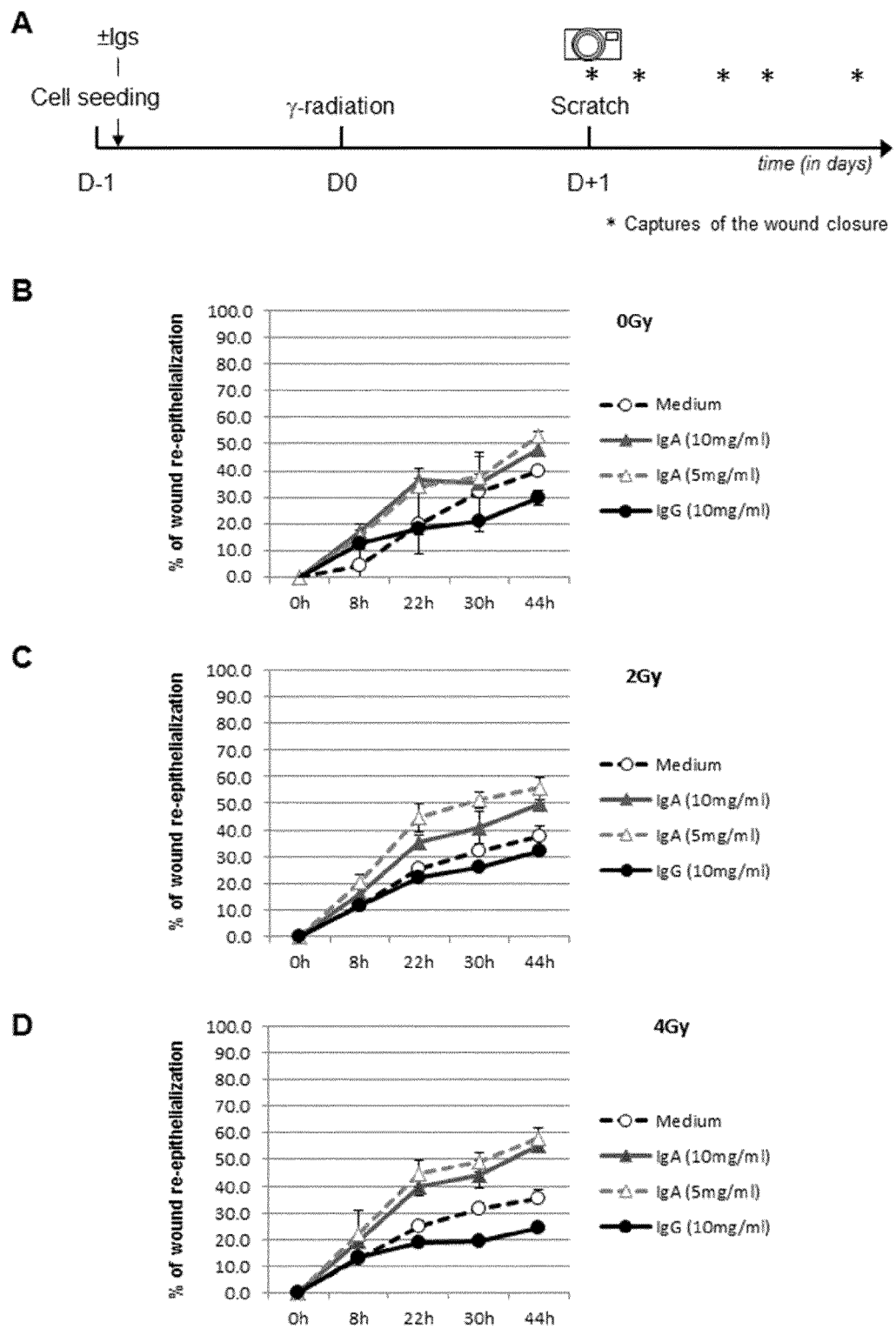

FIG. 14. Wound healing assay using IgA F4. (A) The experiment was performed as depicted in the timeline. (B,C,D) Closure of the artificial gap in the cell monolayer was documented by capturing the images of the scratch at different time intervals and gap size was measured. 100% wound re-epithelialization corresponds to a full recovery of the artificial gap.

Figure 15:
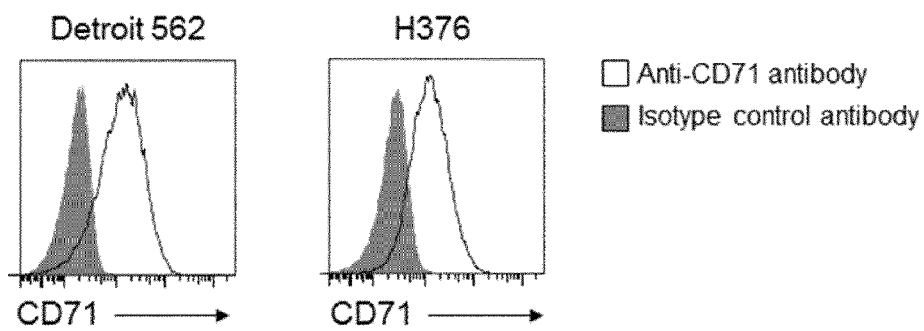
Figure 15:
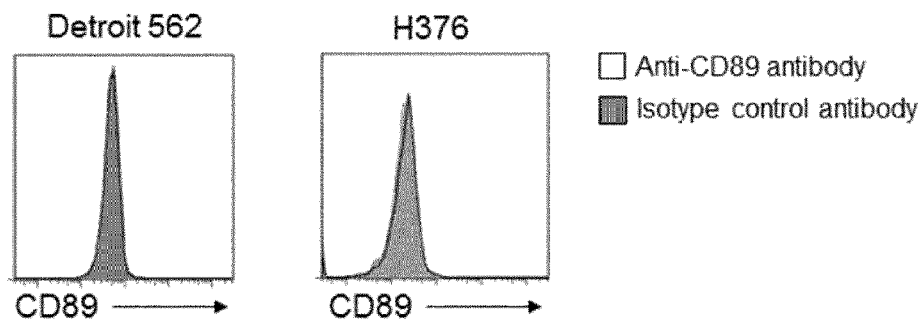

FIG. 15. Analysis of IgA receptors on epithelial cell lines. Stainings for CD71 and CD89 (or relevant isotype controls) were performed on H376 and Detroit cells and analyzed using a flow cytometer.

Figure 16:
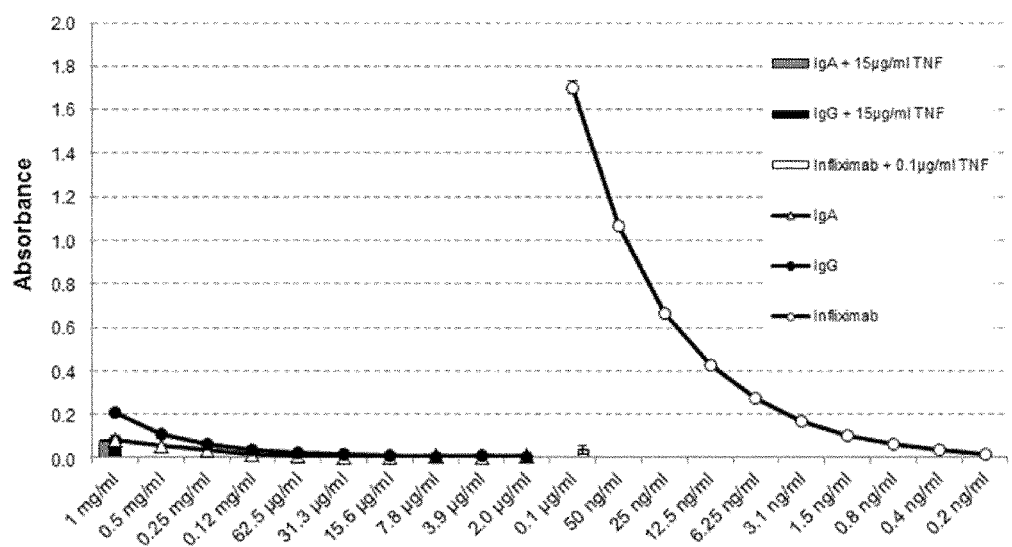

FIG. 16. Anti-TNF activity in IgA F4 and IgG preparations was assessed by ELISA. Wells from an ELISA plate were coated with TNFα (1 µg/ml) and further blocked. Increasing concentrations of IgA F4, IgG and an anti-TNFα antibody (monoclonal, infliximab) were applied to the wells. In some wells, free TNFα was added to inhibit specific binding of the tested antibodies (competition assay; bars). After washes, TNFα-bound immunoglobulins were revealed with HRP-labelled specific secondary antibodies.

EXAMPLES

The study encompassed in the examples shows that immunoglobulins can have a combined antimicrobial and anti-inflammatory/pro-wound healing effect, and are therefore an attractive option for an effective prophylaxis and treatment of mucositis of the alimentary tract, in particular oral mucositis.

To mimic the mucosal epithelial cell layer of the oropharyngeal cavity, epithelial cell lines were used. One example of a suitable cell line for such studies is the human pharyngeal cell line Detroit 562 (ATCC CCL 138). Further suitable cell lines used are H376, a squamous carcinoma cell line derived from the floor of the mouth, and HGF-1, a gingival fibroblast cell line. As an example of a microorganism that is part of the mucosal microflora, we used Moraxella catarrhalis, which is a typical naso- and oropharyngeal pathogen, as well as other bacteria found in the oral microbiota, such as *Streptococcus* species. This model experimental system was considered suitable for preliminary in vitro experiments, because the origin of the cell lines corresponds to the intended (preferred) site of action of orally administered immunoglobulin. Furthermore, Detroit cells have previously been shown to exhibit proinflammatory activation upon exposure with bacteria (live or inactivated whole bacteria or bacterial surface components). *M. catarrhalis*, which is a facultative pathogen, whose only natural habitat is the human pharynx, was chosen, because its capacity to adhere to and penetrate Detroit cells in vitro, and because it induces the secretion of proinflammatory mediators such as IL-6, IL-8, TNFα, MCP-1 and GM-CSF. In addition, specific outer membrane proteins of *M. catarrhalis* (e.g., UspA1 and UspA2) both mediate adherence and invasion, and trigger the proinflammatory cascade by binding to CEACAM1 and TLR2. Isogenic knock-out mutants of these outer membrane proteins are available. UspA1 and UspA2 of *M. catarrhalis* are known immunogens recognized by the human immune system and induce specific plasma and salivary IgA and IgM in healthy individuals. In addition, *Streptococcus* species, in particular *S. mitis* and *S. pneumonia*, were used as typical opportunistic pathogens present in the oral cavity. Thus, this in vitro model is suitable to assess the effects of human immunoglobulin preparations on bacterial adherence and invasion and on bacterial induction of inflammation.

Example 1

Plasma-Derived and Saliva-Derived Immunoglobulin Preparations Comprise Antibodies that Recognize *M. catarrhalis*

To test whether our immunoglobulin preparations could have an anti-microbial effect, we first wanted to establish whether they contain antibodies that recognize a potential pathogen found on mucosal surfaces of the oro-pharyngeal tract. As an example of such a microorganism, we used *M. catarrhalis*.

1.1. Bacterial Strains and Human Cell Lines.

The *M. catarrhalis* strain 25238 was purchased from the American Type Culture Collection (ATCC). The laboratory strain O35E is a middle ear isolate from a child with otitis media. Bacteria were cultured on brain-heart infusion (BHI) agar plates (Difco, Detroit, Mich.) at 37° C. in an 5% $CO_2$ atmosphere or in BHI broth at 37° C. and 200 revolutions per minute (rpm). In some experiments, bacteria were heat-inactivated by resuspension of live bacteria in PBS and incubation at 60° C. for 60 min. The human pharyngeal cell line Detroit 562 (ATCC CCL 138) was maintained in Eagle's minimal essential medium (MEM; Invitrogen, Basel, Switzerland) supplemented with 10% of heat-inactivated fetal calf serum (FCS), 2 mM of L-glutamine, 1 mM sodium pyruvate (Sigma, St. Louis, Mo.), 1× nonessential amino acids (Sigma), 100 U/ml penicillin, and 100 µg/ml streptomycin at 37° C. in 5% $CO_2$.

1.2. Reagents.

Pooled human immunoglobulin isotypes (IgA ("IgA F4" [50 mg/ml], "IgA F5A" [50 mg/ml]) IgG (Privigen® [100 mg/ml] and IgM ("IgM F5A" [10 mg/ml]), respectively) were obtained from CSL Behring, Bern, Switzerland. The IgG preparation is a commercially available human intravenous IgG (IVIG) preparation (Privigen®). The purified human plasma IgA and IgM fractions are experimental products. IgA was produced from plasma by sequential elution of MPHQ column and subsequent separation by affinity chromatography. From the AIEX chromatography step of the IVIg manufacture process of CSL Behring AG (Berne, Switzerland), fraction F4 was obtained after a post-wash of the Macro-Prep High Q (Bio-Rad, Hercule, Calif.) column with 10 mM phosphate/30 mM acetate at pH 6.5 by elution with 55 mM tartrate/5 mM acetate at pH 7.6. Fraction F5 was subsequently eluted with 50 mM phosphate/25 mM citrate at pH 5.0. F4 and F5 were brought to approximately 1 mG/mL in PBS by ultra-/diafiltration, and then depleted of IgG by affinity chromatography using IgSelect resin (GE Healthcare, Glattbrugg, Switzerland). IgA F4 was directly harvested in the flowthrough of the IgSelect chromatography of F4 load. To obtain IgA F5, the IgSelect flowthrough of F5 load was depleted of IgM by affinity chromatography using CaptureSelect Human IgM resin (Bioaffinity Company BAC). Elution of this CaptureSelect Human IgM resin resulted in the IgM F5 fraction used here. IgA F4, IgA F5 and IgM F5 were brought to final concentrations by ultra-/diafiltration.

1.3. Immunoblot Analysis.

Outer membrane protein (OMP) preparations of the strains 25238 and O35E were prepared by the EDTA-buffer method (Murphy T F & Loeb M R (1989) Microb Pathog 6: 159-74) and resolved by SDS-PAGE (10% polyacrylamide) at a protein concentration of 0.5 and 0.4 µg/mm of gel slot in FIGS. 1 and 2, respectively. Gels were subsequently electrotransferred to PVDF membranes (Immobilon-P®, Millipore Corporation, Bedford, Mass.). Immunoblot analysis was performed using monoclonal antibodies (17C7 (Aebi C et al (1997) Infect Immun 65:4367-77), 24B5 (Cope L D et al (1999) J Bacteriol 181: 4026-34), 10F3 (Aebi C et al (1998) Infect Immun 66: 3113-9) [0.5% of mAb supernatant, absolute concentrations not known]) and saliva or the above mentioned pooled human IgA or IgG (0.4 µg/ml) as primary antibody and a 1:4000-diluted goat-anti-human IgA or IgG labeled with horseradish peroxidase (Sigma Corp., St. Louis, Mo.) as secondary antibody. SuperSignal West Pico chemiluminescent substrate (Pierce Chemical Co., Rockford, Ill.) was used for detection of antibody binding.

FIG. 1 demonstrates that OMP of strain ATCC 25238 strongly react with three monoclonal antibodies directed against the major OMP UpA1 (mAb 17C7 and mAb 24B5), UspA2 (mAb1707) and CopB (mAb10F3) similar to strain O35E (Helminen M E et al (1993) Infect Immun 61: 2003-10; Helminen M E et al (1994) J Infect Dis 170: 867-72; Cope L D et al (1999) J Bacteriol 181: 4026-34), from which these mAbs were generated, and which is a standard representative of the major and more clinically relevant phylogenetic lineage 1 of *M. catarrhalis* (Meier P S et al (2005) Vaccine 23: 2000-8).

We subsequently confirmed that human plasma and saliva contain antibodies, which react with *M. catarrhalis* OMP from both strain ATCC 25238 and O35E using a standard immunoblot assay (Stutzman et al (2003) Infect Immun 71: 6793-8). FIG. 2 demonstrates that both human saliva and OMP contain multiple antigens, which are recognized by human IgA (saliva, OMP) and/or IgG.

It was important to first ascertain that strain ATCC 25238 behaved similarly in expressing epithelial cell adhesins (mAbs 17C7 and 25B4) as the standard O35E phylogenetic group 1 strain (Bootsma H J et al (2000) J Infect Dis 181: 1376-87), which is used worldwide as a reference pediatric middle ear isolate of *M. catarrhalis* and was used for the generation of the monoclonal antibodies available. FIG. 1 indicates that this is the case. In addition, as shown in FIG. 2, plasma derived IgA and IgG recognize the same ATCC 25238 outer membrane epitopes, which further validates the usefulness of this strain in our series of experiments. It is of note here that the UspA1 major adhesin (reactive with both the mAbs 17C7 and 24B5) contains domains that react with human fibronectin and with CEACAM 1 (Brooks M J et al (2008) Infect Immun 76: 5322-9) and should thus be able to bind to a large variety of human epithelial cell lines. The generation of distinct bands in immunoblotting supports the notion that antibodies bind outer membrane vesicles by using their specific antigen-binding (Fab) domains.

Example 2

Inhibition of Bacterial Adhesion to Epithelial Cells

To further substantiate the anti-microbial effect of our immunoglobulin preparations, it was tested whether the immunoglobulin preparations were effective in inhibiting the adhesion of M. catarrhalis to pharyngeal epithelial cell line Detroit 562.

The ability of M. catarrhalis to adhere to human epithelial cells in vitro was measured as previously described (Aebi C et al (1998) Infect Immun 66: 3113-9) with the following modifications. Detroit 562 cells (~3×10$^5$ cells per well) grown overnight to a confluent monolayer in 24-well tissue culture plates in MEM supplemented with 0.1% FCS but without antibiotics followed by washing three times in MEM. Bacteria were grown overnight and adjusted to the appropriate multiplicities of infection (MOI). Live bacteria were added to the wells in MEM without FCS supplemented with the appropriate concentrations of immunoglobulins (prepared as described in paragraph 1.2 above) or controls (e.g. proline for IgG assays), but without antibiotics, centrifuged for 5 min at 1,500 rpm, and subsequently incubated for 30 minutes at 37° C. Wells were then washed 5 times in MEM, trypsinized and the suspensions were cultured quantitatively to determine the number of adherent bacteria. Strain O35E.1 (i.e., an isogenic uspA1 adhesin knock-out mutant generated by allelic replacement (Aebi C et al (1998) Infect Immun 66: 3113-9)) was used as positive (i.e., adherence inhibiting) control. Data were expressed as the proportion of bacteria of the original inoculum adhering to the epithelial cells. Each assay was conducted in triplicate and at least three experiments were performed, resulting in at least 9 data points per condition investigated. Cell viability was ascertained morphologically, by trypan blue exclusion, and a commercial LDH assay (BioChain Institute, Inc., Hayward, Calif.).

Both IgA F4 (FIG. 3) and IgA F5 (FIG. 4) significantly inhibited adherence at a concentration of 5 mg/ml. Adherence of the positive controls O35.1 and O35.1 supplemented with 5 mg/ml of IgA was significantly lower. Inhibition of adherence by pooled human plasma IgG was significant overall, but none of the inter-column differences reached statistical significance although FIG. 5 suggests an IgG concentration-dependent inhibitory effect. The IgM F5A fraction, on the other hand, demonstrated a strong adherence-inhibiting effect as shown in FIG. 6.

IgA F4 and IgA F5 were found to significantly inhibit adherence to Detroit cells at a concentration of 5 mg/ml (see FIG. 3 and FIG. 4). There appeared to be a dose-effect curve. Adherence of the positive control strains O35.1, an isogenic mutant lacking expression of the major adhesin UspA1, also was significantly lower (significance not indicated). These findings indicate that plasma IgA is—at a concentration approximately one $\log_{10}$ above physiologic saliva concentrations—capable to inhibit binding of M. catarrhalis to pharyngeal epithelial cells in vitro. These data support its potential as a neutralizing "mucosal" antibody preventing the pro-inflammatory effects of bacterial surface components (e.g., OMP, LOS). Similar findings were documented for purified plasma IgM F5A (FIG. 6). An analogous trend (FIG. 5) was also observed for plasma IgG (Privigen®), although no statistical significances were obtained. It is noteworthy to mention that bound IgG (as well as IgM) strongly activates human complement and that bacterial binding with subsequent killing or opsonization may be undesirable in preventing mucositis. However, it is not known whether and to what extent complement is active in the human cavity.

Example 3

Inhibition of Bacterial Invasion of Epithelial Cells by Immunoglobulins

As previously shown (Spaniol V et al (2008) Microbes Infect 10: 3-11), M. catarrhalis is able to penetrate epithelial cells and even localize in the submucosal pharyngeal soft tissue in vivo in children and young adults (Heiniger N et al (2007) J Infect Dis 196:1080-7). Thus, we investigated the potential of human immunoglobulins to inhibit the penetration of pharyngeal epithelial cells in vitro to further demonstrate the potential benefit of immunoglobulin preparations.

Bacterial invasion was estimated using a gentamicin protection assay as previously described (Spaniol V et al (2008) Microbes Infect 10: 3-11) with the following modifications. Cells were prepared in medium without antibiotics. After washing, bacteria were added at a MOI of 30 together with the indicated concentration of each immunoglobulin prepared as described in paragraph 1.2 above, centrifuged for 5 min at 1,500 rpm and incubated for 3 h at 37° C. in 5% $CO_2$. To determine the number of intracellular bacteria, the infected monolayer was washed three times in PBS and treated with gentamicin sulfate (200 µg/ml) for 2 h at 37° C. After washing, cells were detached from the plastic surface by treatment with 0.25% trypsin-EDTA, lysed by the addition of 1% saponin, and serially diluted in PBS for quantitative bacterial culture. Invasion ratios were calculated by dividing the number of cfu recovered after gentamicin exposure by the number of cfu inoculated.

FIG. 7 demonstrates that IgA F4 at a concentration of 10 mg/ml significantly inhibited the penetration of Detroit 562 pharyngeal cells in comparison to 0.1 mg/ml. Comparison of 10 mg/ml with the negative control (MEM-PBS) failed to reach significance. Similarly, human pooled plasma IgG (Privigen®) at 10 mg/ml significantly inhibited invasion in comparison with the MEM-PBS negative control. This was also true for the plasma IgM F5, which at 5 mg/ml demonstrated a significant inhibition of invasion in comparison with the MEM-PBS control and the lowest IgG concentration of 0.1 mg/ml. As a measure of dispersion in FIGS. 7 to 9 we used the standard error of the mean (SEM). We also are forced to refrain from presenting "positive" controls completely failing penetration of Detroit cells, because no such bacteria were available.

More and more classic extracellular pathogens have recently been found to be able to penetrate or transcytose across the mucosal epithelial cell layer, e.g. nontypeable Haemophilus influenzae Eldika, N & Sethi S (2006) Curr Opin Pulm Med 12: 118-24), Staphylococcus aureus Que Y A et al (2005) J Exp Med 201: 1627-35), etc. Intracellular persistence may be a means of evading mucosal immunity and to access the host's subepithelial and—ultimately—vascular space. This may be of particular relevance in patients with febrile neutropenia and mucositis. We measured immunoglobulin-mediated inhibition of epithelial penetration using an established gentamicin protection assay and found that all three isotypes were able to inhibit penetration of Detroit cells. In the cases of IgA F4 (FIG. 7) and IgM F5A (FIG. 9), significant inhibition was observed at 10 mg/ml and 5 mg/ml, respectively. Again, a similar trend, although not statistically significant, was found for plasma IgG (FIG. 8).

Example 4

Modulation of Epithelial Cytokine/Chemokine Release by Immunoglobulins

To show the potential for anti-inflammatory effects of the immunoglobulins, it was investigated whether the immunoglobulin preparation had an effect on cytokine/chemokine release by epithelial cells.

Detroit cell monolayers were prepared and stimulated with different concentration of M. catarrhalis OMP (see Example 1.3, for OMP preparation) in presence of increasing concentrations of IgA F4. Negative controls consisted of medium with or without OMP. Individual supernatants were collected at time 0 and 24 hours after stimulation, and then kept at −80° C. until analysis. In the present experiment samples were incubated for 16 hours overnight before detection. As a matrix solution we used RPMI-1640 cell culture medium (Sigma, R8758) in 0.1% FCS. After preparing the samples the data were acquired with a Bioplex 200 analyzer (BioRad). Preparation of Detroit cells, exposure to various concentrations of immunoglobulins and OMP were performed at the Institute for Infectious Diseases, University of Bern. The determination of cytokines/chemokines was conducted at CSL Behring, Bern.

At time 0, Detroit cells received a fresh medium supplemented with or without OMP and different concentrations of IgA F4. For this reason, and as shown in FIG. 10A,B,C, almost no cytokine could be detected at this time in the supernatants. At 24 h, without any OMP, Detroit 562 cells secreted detectable levels of MCP-1, IL-8 and IL-6 (FIG. 10A,B,C). MCP-1 is a key chemokine which regulate recruitment of monocytes/macrophages. It is involved in many diseases (Deshmane S L et al (2009) J. Int. & Cyt. Res. 29, 6, 313-326). IL-8, or neutrophil chemotactic factor, is a chemokine which recruits neutrophils to tissue. It is also associated to inflammation in the buccal cavity (Ertugrul A S et al (2013) J Periodont Res; 48: 44-51). Lastly, Also, IL-6 is an important mediator of inflammation and has been shown to be induced in irradiated fibroblasts (Brach M A et al (1993) J. Biol. Chem. 268:8466-8472; Rincon M (2012) Trends Immunol. 33 (11) 571-577). Importantly, addition of OMP in the medium increased MCP-1, IL-8 and IL-6 production by around 10-, 3- and 7-fold respectively. Moreover, while low amounts of IgA F4 had almost no effect on OMP-induced chemokine/cytokine production, 10 mg/ml IgA strikingly reduced MCP-1, and to a lesser extent, IL-8 and IL-6 secretion.

To support these results, we aimed at testing IgA F4 activity on additional cell lines. The tissue of the floor of the mouth represents one of the tissues which are injured during the course of oral mucositis. We found a new cell line, H376 (human oral squamous cell carcinoma; HPACC 06092005), which originates from the floor of the mouth. In addition to H376, we chose to study gingival fibroblasts (HGF-1 cell line; ATCC® CRL-2014™) as they are situated underneath the buccal epithelial cells and will sense inflammation in the course of oral mucositis.

In the following experiments, we analyzed the cytokine profile of H376 and HGF-1 cells.

Cell monolayers were prepared in the presence of 2 concentrations of IgA F4 (5 and 10 mg/ml prepared in MEM). Negative controls consisted of medium alone (pure MEM cell culture medium, Life technologies, 51200-046). Individual supernatants were collected at 24 hours. HGF-1 cells were stimulated with pro-inflammatory cytokines (e.g. recombinant IL-1β and TNFα, both at 50 ng/ml; from Milteni (130-093-893) and Peprotech (300-01A) respectively) which are known to stimulate fibroblasts. After stimulation, supernatants were then kept at −80° C. until analysis. As a matrix solution we used MEM. After preparing the samples the data were acquired with a Bioplex 200 analyzer (BioRad).

H376 cells secreted IP-10 which is an IFN-γ-induced protein associated with inflammation (Liu M et al (2011) Cytokine growth Factor Rev. 22(3), 121-130) and G-CSF which represents an inflammatory mediator capable to recruit neutrophils at inflammatory sites (Suzuki S (2002) Blood 99: 1863-1865)(FIG. 11A,B). In FIGS. 11A and B, we show that treatment of H376 cells with IgA 5 mg/ml strongly reduced both IP-10 and G-CSF production by about 50%. Increasing IgA concentration to 10 mg/ml did not further reduce G-CSF production but reduced IP-10 production slightly better than IgA at 5 mg/ml (FIG. 11A,B). H376 cells are tumor cells and might have an activated phenotype. We cannot rule out that both IP-10 and G-CSF levels might not be as high as in primary buccal epithelial cells.

HGF-1 are gingival fibroblasts. They did not produce any IP-10 at steady state (FIG. 11C). However, there was a clear induction of IP-10 production when inflammatory molecules such as IL-1β and TNF-α were applied in their medium (pure MEM). TNFα was more potent in IP-10 induction than IL-1β, at equivalent concentrations. In both conditions, addition of IgA at the time of the stimulation strongly reduced IP-10 production with the highest IgA F4 concentration showing the strongest reduction. Nevertheless, IgA F4 at 5 mg/ml showed a very similar immunosuppressive effect (FIG. 11c).

In summary our data are the first to show that IgA F4 exerts an immunosuppressive effect on cells which are not myeloid cells (e.g. epithelial cells). This is very valuable information as during the course of oral mucositis, pro-inflammatory chemokines and cytokines will be up-regulated in response to ionizing radiation and/or bacterial colonization by epithelial cells and fibroblasts. These results indicate that during the course of oral mucositis, IgA can potentially target its immunosuppressive effect on a wide range of cell subsets (e.g. neutrophils, macrophages, epithelial cells, etc).

Example 5

Inhibition of Adherence, Invasion and Modulation of Epithelial Cytokine/Chemokine Release Induced by Bacteria Other than M. catarrhalis by Immunoglobulins In similar experiments, as described in Examples 1-4, other microorganisms such as bacteria other than M. catarrhalis, or fungi, are investigated. They include but are not limited to pathogenic and opportunistic pathogenic species such as Escherichia coli, Staphylococcus aureus,

*Pseudomonas aeruginosa, Streptococcus viridans* group, *Streptococcus pneumonia, Enterococcus faecalis/faecium, Klebsiella pneumonia, Enterobacter aerogenes, Haemophilus influenza, Stenotrophomonas maltophilia, Streptococcus pyogenes, Streptococcus mitis, Candida albicans*, and many species of anaerobic bacteria. Similar results as described in Examples 1-4 are obtained: IgA preparations contain specific antibodies against the above mentioned bacteria or fungi; adherence and invasion of epithelial cells are inhibited; inflammatory cytokine response is inhibited. Similar results are obtained with other epithelial cell lines, representative of the mucosal lining of the gastro-intestinal tract and the colon.

Example 6

Prevention of Mucositis in an Animal Model

Appropriately formulated Immunoglobulin preparations are tested in animal models of oral mucositis. Immunoglobulin is applied prophylactically and following the induction of mucositis by concurrent chemo- and radiotherapy (CCRT) in a CD89-transgenic mouse model adapted from Ryu at al (J. Radiat. Res., 51, 595-601, 2010). We measure the effects of immunoglobulin treatment on the extent and severity of the oral mucositis, but also on factors associated with wound-healing and the resolution of the tissue damage resulting from CCRT. Actual indicators of oral mucositis severity are loss of body weight, atrophy of the tongue and buccal mucosa (epithelial thickness). Furthermore, the treatment effects are assessed by measuring epithelial layer thickness, number of basal cells in mucosa, histological quantification of the proliferation marker KI-67, mRNA transcripts (by in situ hybridization and RT-PCR of tissue samples) and protein expression of growth factors like KGF, epithelial growth factor, fibrocyte growth factors, vascular endothelial growth factors A, etc. Such analyses will yield information about the downmodulation of intracellular proinflammatory cascades as a result of immune exclusion and potentially also due to the direct interaction of IgA with CD89-expressing cells. Mice treated with IgA lose less body weight and their tongue and buccal mucosa is less severely affected than in non-treated animals. Mice treated with secretory-like IgA are even better protected.

Alternatively, hamster models of oral mucositis are used, similar as described in Watkins et al (Oral Dis 2010, 16:655-660). Appropriately formulated IgA preparations (or vehicle solution for control) are given prophylactically (e.g. starting at day−3) three times daily to Syrian Golden Hamsters for the entire duration of the study up to day 28. In a model of acute radiation-induced mucositis, on day 0 one everted buccal cheek pouch is irradiated (40 Gy), the other cheek pouch is left untreated for control. Alternatively, in a model of fractionated radiation-induced mucositis, a cumulative dose of 60 Gy is applied, partitioned into eight fractions of 7.5 Gy as described in (Watkins, Oral Dis 2010, 16:655-660). In yet another model of combination cisplatin and acute radiation-induced mucositis, disease is induced by a combination of cisplatin (5 mg/kg) and 35 Gy radiation on day 0. Clinical evaluation of oral mucositis and monitoring of body weight is done daily, starting on Day 6 until the end of the study, typically on Day 28. The scoring system is described in (Watkins Oral Dis, 2010 16:655-660). In addition, tissue and plasma samples are collected and appropriately processed throughout the study for histological analyses, determination of inflammatory markers in plasma and for gene expression studies of various tissues. Untreated/vehicle treated animal develop oral mucositis, disease peaks around day 16-18, spontaneous healing, evidenced by a regression of the mucositis, starts around day 18-20. Animals treated with IgA have significantly lower mucositis scores compared to control animals and lose less weight, paralleled by less severe histological findings and reduced levels of inflammatory markers (including but not limited to inflammatory cytokines and chemokines). Reduction of inflammation and promotion of wound-healing is confirmed at the level of mRNA expression by gene-expression analysis techniques. Treatment with secretory-like IgA is even more effective.

Example 7

Inhibition of Adherence of Opportunistic Pathogens to Buccal Epithelial Cells To corroborate and further strengthen our data on the anti-microbial effect of our immunoglobulin preparations presented in example 2, we tested the capacity of IgA to interfere with bacterial adherence to H376 epithelial cells.

Buccal microflora is composed of a large variety of bacterial strains with a predominance for the Firmicutes phylum (The Human Microbiome Project Consortium (2012) Nature 486:207-214) (Dewhirst F E (2010) J. Bacteriol 192:5002-5017). Importantly, non-encapsulated *Streptococcus pneumoniae* and *Streptococcus mitis* (both from the Firmicutes phylum) are genetically very close. *S. mitis* is known to represent the major oral opportunistic pathogen and can potentially lead to infection when the epithelial barrier is broken as it may typically happen in patients with oral mucositis. Non-encapsulated *S. pneumoniae* adhere well to epithelia and can cause mucosal infections including conjunctivitis, but not invasive disease. Thus both *S. pneumoniae* R6 and *S. mitis* are useful model organisms for studying the interaction between bacteria and the oral mucosal epithelium in the context of this project.

The ability of bacterial isolates to adhere to human epithelial cells in vitro was measured as previously described in example 2 and in the literature (Aebi C et al (1998) Infect Immun 66: 3113-9) with the following modifications. H376 cells (~$3 \times 10^5$ cells per well) were grown overnight to a confluent monolayer in 24-well tissue culture plates in MEM supplemented with 0.1% FCS but without antibiotics followed by washing three times in MEM. Bacteria were grown overnight and adjusted to the appropriate multiplicities of infection (MOI). Live bacteria were added to the wells in MEM without FCS supplemented with the appropriate concentrations of immunoglobulins (prepared as described in paragraph 1.2 above) or controls (e.g. proline for IgG assays), but without antibiotics, centrifuged for 5 min at 1,500 rpm, and subsequently incubated for 30 minutes at 37° C. Wells were then washed 5 times in MEM, trypsinized and the suspensions were cultured quantitatively to determine the number of adherent bacteria. Data were expressed as the proportion of bacteria of the original inoculum adhering to the epithelial cells. Each assay was conducted in triplicate and at least three experiments were performed, resulting in at least 9 data points per condition investigated. Cell viability was ascertained morphologically, by trypan blue exclusion, and a commercial LDH assay (BioChain Institute, Inc., Hayward, Calif.).

As shown in FIG. 12A, *S. pneumoniae* R6 adhered very well to the H376 cells which originate from the floor of the mouth. After washing, more than 60% of the bacteria were still adherent to the cells. Importantly, addition of IgA F4, at 2 mg/ml was sufficient to strikingly block S. pneumoniae R6 adherence on epithelial cells. Approximately 75% of the bacteria could be prevented from adhering to the cells. Increasing IgA doses showed slightly more inhibition of bacterial adherence. In FIG. 12B, adherence of S. mitis on H376 was tested. We found that S. mitis bound to epithelial cells, to a lesser extent than S. pneumoniae R6. However, IgA F4 clearly inhibited S. mitis adherence with a maximal effect at 5 mg/ml. Thus administration of IgA F4 in the buccal cavity of patients displaying oral mucositis symptoms may protect buccal epithelia from opportunist pathogen colonization.

Example 8

IgA Protects Epithelial Cells from γ-Ionizing Radiation Induced Cytotoxicity

Radiotherapy used to treat tumor-bearing patients targets proliferating cells (tumor cells for instance). By generating DNA breaks and reactive oxygen species, γ-ionizing radiations generally induce tumor cell death. While it is believed that cells of the buccal epithelia are more resistant to irradiation because of their low turn-over, repeated irradiations can still induce cytotoxicity to these cells. To investigate if IgA has an impact on cell survival after ionizing radiation, we irradiated H376 and measured cell cytotoxicity after 24 h.

As depicted in FIG. 13A, H376 were seeded at $3 \times 10^4$ cells/well (96 well plate) in MEM (80 µl) and kept two hours at 37° C. Then IgA F4 (5 or 10 mg/ml) and/or MEM were added to the wells to reach a final volume of 100 µl (triplicates). A day later, cells were irradiated with 4 Gy and returned to 37° C. 24 h after irradiation, cell cytotoxicity was assessed using the CytoTox-Glo™ Cytotoxicity Assay kit (Promega, G9291). This kit measures the amount of intracellular proteases released during the course of cell death.

As shown in FIG. 13B, more than 30% of H376 died after receiving ionizing radiation. Prophylactic treatment of the H376 cells with IgA F4 reduced this cytotoxicity in a dose dependent manner. IgA at 10 mg/ml inhibited cell death at 24 h by almost 50% and IgA at 5 mg/ml by almost 30%. Therefore, addition of IgA to epithelial cells provided a survival advantage and may reduce effects of repeated irradiation on patient epithelia.

Example 9

Beneficial Effect on Wound Re-Epithelialization

Although controlling bacterial colonization and inflammatory signals during oral mucositis is of relevance, it is becoming evident that the reduction of oral mucositis symptoms requires a rapid wound closure after ulceration of the buccal epithelium. KGF plays an important role in wound re-epithelialization. This is one of the reasons why KGF is currently one of the few authorised drugs for use in the treatment of oral mucositis. To further delineate the potential role of IgA during oral mucositis, we tested IgA on wounded epithelia. To reproduce potential damaging effect of irradiation on cell epithelia in vitro, we irradiated cell monolayers before using them in a scratch assay.

The main assay used to test wound healing is the common scratch assay. It consists of scratching a cell monolayer and capturing images over time in order to measure the closure of the artificial wound. As presented in FIG. 14A, we seeded ~$3 \times 10^5$ H376 cells per well (24-well plate) in MEM (500 µl final volume) and plates were kept at 37° C. for 2 h. Then immunoglobulins (e.g. IgA or IgG or medium control) were added to the wells and plates were placed for a further twenty-two hours at 37° C. At this step, plates were irradiated at 2 Gy, 4 Gy or left untreated, and returned to 37° C. 24 h later, a scratch was made with a P1000 tip through the cell monolayer of each well. To prevent scratched cells from falling into the artificial gap, medium was removed, cell monolayer was washed once with MEM and then MEM supplemented or not with immunoglobulins was added to the wells. Images were captured at different time points using a microscope and the size of the gap was measured. 100% wound re-epithelialization corresponds to a full recovery of the artificial wound.

IgA F4 was tested at two doses (10 mg/ml and 5 mg/ml) while IgG was used at 10 mg/ml. Interestingly, at steady state, IgA showed a slightly positive effect on the artificial gap closure (FIG. 14B). On the contrary, IgG seems to slow down wound closure. When irradiated cell monolayer were scratched, the role of IgA became clearer (FIGS. 14C and D). IgA F4 maintained migration and division of irradiated H376 cells while untreated irradiated cells did not cover the artificial gap with the same speed. Moreover, the IgA effect was stronger when cells were irradiated with 4 Gy. A negative effect of IgG on the epithelial cells was observed when cells were irradiated at 2 Gy and 4 Gy (FIG. 14C,D).

Example 10

Specific Binding of IgA to Epithelial Cells

To gain information on the potential mechanism by which IgA regulate epithelial cell function over the course of bacterial stimulation and wound re-epithelialization, we analyzed cell surface expression of IgA receptors on both Detroit 562 and H376 epithelial cells.

Several receptors have been described to bind IgA. They are CD89, CD71 (transferrin receptor), ASGP-R, FCAMR (Fcα/mR, CD351) and pIgR (CD300e) (Monteiro et al (2003) Annu. Rev. Immunol. 21:177-204). CD89 is expressed on myeloid cells while ASGP-R, FCAMR and pIgR are present on hepatocytes, on B-lymphocytes and macrophages, and on intestinal epithelial cells respectively. Only CD89 binds IgA with high specificity.

Because many cell types requires iron uptake from transferrin which is driven by binding of transferrin on its receptor (e.g. CD71), CD71 is thus potentially expressed on many cell types except highly differentiated cells (Pomka P et al (1999) IJBCB 31, 1111-1137). However, its level varies considerably from cell to cell. Up to now, CD71 has been shown to bind both monomeric IgA and secretory IgA (Moura et al (2001) J. Exp. Med. 194, 4, 417-425). It is therefore a potential target for IgA on buccal epithelial cells.

To control expression of this receptor, we gently detached PBS 1×-washed H376 and Detroit 562 cells with accutase (eBioscience) for 10 minutes at 37° C., washed them with PBS 1× and stained them in PBS 1× on ice for 30 minutes using an anti-human CD71 (BD Biosciences, clone A59) antibody. An isotype control antibody was used to assess the level of background fluorescence. CD89, which is only expressed on myeloid cells, was used as a negative control (BD Biosciences, clone M-A712). After two washing steps, samples were run on a FACS Canto II flow cytometer (Becton Dickinson).

As shown in FIG. 15, we found that both Detroit 562 and H376 epithelial cells clearly expressed the transferrin receptor. On the contrary, and as expected, CD89 was not detected on epithelial cells Example 11

IgA F4 Preparations do not React with TNFα

Over the last few years, generation of immunoglobulins (e.g. monoclonal antibodies) to target and/or inhibit key proteins responsible for inflammation or promoting tumor development strongly increased. In chronic diseases as well as auto-immune diseases, anti-TNFα-specific antibodies have been shown to dampen inflammation in the treated patients.

As shown in example 4 (FIGS. 10 and 11), IgA down-regulated production of pro-inflammatory molecules by epithelial cells). To rule out the involvement of anti-TNF activity in the observed anti-inflammatory effects of IgA we determined the levels of TNFα specific antibodies in our polyclonal IgA and IgG preparations.

TNF-α was coated at 1 μg/ml in PBS pH7.4 (50 μL per Well) in 96-well plates (sample plate) (Nunc Maxisorb) for 2 h at 37° C. Wells were then washed once with 300 μl Wash Buffer (1×PBS, 0.05% (v/v) Tween-20) and blocked with Smart Block (Candor Bioscience) for 2 hour at 37° C. In parallel, a binding control plate (blank plate) without coated TNF-α was prepared. Following a wash step Ig samples (IgA F4/IgG Privigen/Infliximab) were diluted in Low-CrossBuffer (LCB) (Candor Bioscience). In some wells, free TNF-α was added to inhibit antibody binding. Samples (100 μl) were pipetted into the plates and incubated 2 hour at 37° C. Following incubation, wells were washed three times and plates incubated for 30 minutes at 37° C. with the relevant secondary antibodies: polyclonal rabbit anti-human IgG-HRP (Dako; 0.5 μg/ml) or polyclonal rabbit anti-human IgA HRP (Dako; 0.5 μg/ml) in antibody buffer (LCB). Wells were washed four times as before and subsequently developed with ultra-sensitive TMB (Fitzgerald). The reaction was stopped with 1M hydrochloric acid (Merck) and absorbance was measured at 450 nm by EnVision Multilabel Reader (Perkin Elmer).

FIG. 16 demonstrates that both our IgG and IgA F4 preparations contained negligible amounts of anti-TNFα antibodies. At equivalent concentration, IgA and IgG are respectively $1.2 \times 10^6$ and $1.1 \times 10^5$ fold less reactive to TNFα than the anti-TNFα specific antibody Infliximab), Thus, IgA immunosuppressive activity is TNFα independent of anti-TNFα activity.

---

The invention claimed is:

1. A method for the prevention or treatment of mucositis of the alimentary tract comprising:
administering topically to a human subject an effective amount of a composition comprising an effective amount of immunoglobulin derived from pooled human plasma to prevent or treat mucositis of the alimentary tract,
with the proviso that the plasma derived immunoglobulin is not a pure anti-TNF antibody or immunoglobulin enriched for anti-TNF or purified from a human or animal donor immunized with TNF-α.

2. The method of claim 1, wherein the mucositis of the alimentary tract is oral mucositis.

3. The method of claim 2, wherein the patient is undergoing chemotherapy and the patient becomes neutropenic.

4. The method of claim 1, wherein the immunoglobulin comprises IgA or IgM or a combination thereof.

5. The method of claim 3, wherein the immunoglobulin comprises J chain-containing IgA.

6. The method of claim 1, wherein the composition also comprises secretory component.

7. The method of claim 6, wherein the secretory component is recombinant secretory component.

8. The method of claim 1, wherein the composition comprises J-chain containing IgA combined with a protein that is secretory component or a functional variant thereof.

9. The method of claim 1, wherein the composition comprises J-chain containing IgA combined with a protein that is secretory component or a functional variant thereof in combination with another immunoglobulin.

10. The method of claim 1, wherein the composition is formulated to provide a long contact time with the mucosal area affected or at risk of becoming affected by mucositis.

11. The method of claim 10, wherein the composition formulation is selected from a cream, a gel, a syrup, a jelly, a solid form which dissolved near the affected mucosa, or combinations thereof.

12. The method of claim 1, wherein the topical application to the mucosa promotes mucosal wound healing.

13. The method of claim 1, wherein the topical application to the mucosa exerts an anti-inflammatory effect.

14. The method of claim 13, wherein the anti-inflammatory effect is
(a) inhibition of pro-inflammatory cytokine expression; and/or
(b) stimulation of the expression of anti-inflammatory cytokines.

15. The method of claim 1, wherein the subject is a subject at risk of developing mucositis of the alimentary tract.

16. The method of claim 15, wherein the subject at risk is a cancer patient who developed mucositis as a result of a previous chemotherapy and/or radiotherapy treatment.

17. The method of claim 15, wherein the administration of the composition commences when the patient's neutrophil count starts declining.

18. The method of claim 17, wherein the treatment is maintained for the period where the patient's neutrophil count is below normal.

19. The method of claim 1, wherein the composition is administered to the subject up to 6 times per day.

20. The method of claim 1, wherein the composition comprises an additional effective agent for the treatment of mucositis, or wherein the patient is also using another agent.

21. The method of claim 15, wherein the subject at risk is a cancer patient undergoing chemotherapy and/or radiotherapy.

22. The method of claim 20, wherein the another agent is an antiseptic mouthwash.

23. The method of claim 1, wherein said composition is applied topically in the mouth of a patient having oral mucositis to improve symptoms of said oral mucositis.

24. The method of claim 1, wherein the subject is a cancer patient about to undergo chemotherapy and/or radiotherapy.

25. The method of claim 1, wherein active ingredient(s) in the composition consist essentially of components derived from pooled human plasma including said immunoglobulin.

26. The method of claim 1, wherein active ingredient(s) in the composition consists essentially of said immunoglobulin derived from pooled human plasma.

27. The method of claim 24, which comprises the further step of subjecting the cancer patient to chemotherapy and/or after administration of a composition comprising an effective amount of immunoglobulin derived from pooled human plasma.

28. A method for the treatment of oral mucositis comprising:
   oral/buccal administration to a human subject of an effective amount of a composition comprising an effective amount of immunoglobulin derived from pooled human plasma to treat oral mucositis, with the proviso that the plasma derived immunoglobulin is not a pure anti-TNF antibody or immunoglobulin enriched for anti-TNF or purified from a human or animal donor immunized with TNF-$\alpha$.

* * * * *